(12) United States Patent  (10) Patent No.: US 9,277,944 B2
Beyar et al.  (45) Date of Patent: *Mar. 8, 2016

(54) INSTRUMENTATION KIT FOR DELIVERING VISCOUS BONE FILLER MATERIAL

(75) Inventors: Mordechay Beyar, Caesarea (IL); Oren Globerman, Kfar-Shemaryahu (IL)

(73) Assignee: DePuy Synthes Products, Inc., Raynham, MA (US)

( * ) Notice: Subject to any disclaimer, the term of this patent is extended or adjusted under 35 U.S.C. 154(b) by 610 days.

This patent is subject to a terminal disclaimer.

(21) Appl. No.: 13/418,448

(22) Filed: Mar. 13, 2012

(65) Prior Publication Data

US 2012/0226285 A1 Sep. 6, 2012

Related U.S. Application Data

(63) Continuation of application No. 12/296,538, filed as application No. PCT/IL2007/000484 on Apr. 17, 2007, now Pat. No. 8,147,500.

(60) Provisional application No. 60/793,259, filed on Apr. 20, 2006, provisional application No. 60/825,609, filed on Sep. 14, 2006.

(51) Int. Cl.
*A61B 17/58* (2006.01)
*A61B 17/70* (2006.01)
(Continued)

(52) U.S. Cl.
CPC ......... *A61B 17/7098* (2013.01); *A61B 17/8811* (2013.01); *A61B 17/8819* (2013.01); *A61B 17/8855* (2013.01); *A61F 2/44* (2013.01)

(58) Field of Classification Search
CPC ........... A61B 17/7098; A61B 17/8811; A61B 17/8819; A61B 17/8855; A61F 2/44

USPC .................. 606/192, 90, 92–94, 86 A, 86 R; 604/93.01, 272, 224, 227, 96.01; 623/17.16; 600/207
See application file for complete search history.

(56) References Cited

U.S. PATENT DOCUMENTS 3,875,595 A 4/1975 Froning
4,488,549 A 12/1984 Lee
(Continued)

FOREIGN PATENT DOCUMENTS

EP 1407730 4/2004
FR 2764795 12/1998
(Continued)

OTHER PUBLICATIONS

Australian Examiner's Report from AU Appl. No. 2004277963, dated Nov. 14, 2007.
(Continued)

*Primary Examiner* — Pedro Philogene
(74) *Attorney, Agent, or Firm* — Nutter McClennen & Fish LLP

(57) ABSTRACT

A bone filler delivery system comprises a longitudinal channel incorporates a perforated segment at least partially along, at or near its distal end. The channel can be sealed at its distal end so the filler material may be delivered only by the lumen and through the perforated segment. Optionally, said system comprises a permeable bag capable of being inserted into a bone while in collapsed configuration and then expanded when filled with bone voids filler. The mesh structure is designed to allow such permeable bag to expand to a predetermined size or shape under certain pressures and allows exudation of bone void filler through its walls. Extracting the permeable bag out of a treated body promotes flow of bone void filler through its pores into cancellous bone and/or cavity in the bone. The procedure promotes height restoration of the bone and introduces filler in a controlled manner.

26 Claims, 21 Drawing Sheets

(51) Int. Cl.
*A61B 17/88* (2006.01)
*A61F 2/44* (2006.01)

(56) References Cited

U.S. PATENT DOCUMENTS

| | | | |
|---|---|---|---|
| 4,627,434 A | 12/1986 | Murray | |
| 4,772,287 A | 9/1988 | Ray et al. | |
| 4,969,888 A | 11/1990 | Scholten et al. | |
| 5,015,255 A | 5/1991 | Kuslich | |
| 5,108,404 A | 4/1992 | Scholten et al. | |
| 5,133,755 A | 7/1992 | Brekke | |
| 5,443,514 A | 8/1995 | Steffee | |
| 5,465,711 A | 11/1995 | Moll et al. | |
| 5,549,679 A | 8/1996 | Kuslich | |
| 5,562,736 A | 10/1996 | Ray et al. | |
| 5,571,189 A * | 11/1996 | Kuslich | 623/17.12 |
| 5,679,723 A | 10/1997 | Cooper et al. | |
| 5,702,449 A | 12/1997 | McKay | |
| 5,720,726 A | 2/1998 | Marcadis et al. | |
| 5,824,084 A | 10/1998 | Muschler | |
| 5,865,845 A | 2/1999 | Thalgott | |
| 5,888,220 A | 3/1999 | Felt et al. | |
| 5,968,098 A | 10/1999 | Winslow | |
| 6,048,343 A | 4/2000 | Mathis et al. | |
| 6,048,346 A | 4/2000 | Reiley et al. | |
| 6,066,154 A | 5/2000 | Reiley et al. | |
| 6,171,610 B1 | 1/2001 | Vacanti et al. | |
| 6,187,048 B1 | 2/2001 | Milner et al. | |
| 6,241,734 B1 * | 6/2001 | Scribner et al. | 606/93 |
| 6,248,110 B1 | 6/2001 | Reiley | |
| 6,248,131 B1 | 6/2001 | Felt et al. | |
| 6,258,094 B1 | 7/2001 | Nicholson et al. | |
| 6,280,456 B1 | 8/2001 | Scribner et al. | |
| 6,332,894 B1 | 12/2001 | Stalcup et al. | |
| 6,368,351 B1 | 4/2002 | Glenn et al. | |
| 6,375,655 B1 | 4/2002 | Zdeblick et al. | |
| 6,413,278 B1 | 7/2002 | Marchosky | |
| 6,425,923 B1 | 7/2002 | Stalcup et al. | |
| 6,447,514 B1 | 9/2002 | Stalcup et al. | |
| 6,582,446 B1 | 6/2003 | Marchosky | |
| 6,592,625 B2 | 7/2003 | Cauthen | |
| 6,595,998 B2 | 7/2003 | Johnson et al. | |
| 6,679,890 B2 | 1/2004 | Margulies et al. | |
| 6,695,760 B1 | 2/2004 | Winkler et al. | |
| 6,712,853 B2 | 3/2004 | Kuslich | |
| 6,726,691 B2 | 4/2004 | Osorio et al. | |
| 6,730,095 B2 | 5/2004 | Olson et al. | |
| 6,740,093 B2 * | 5/2004 | Hochschuler et al. | 606/94 |
| 6,752,809 B2 | 6/2004 | Gorek | |
| 6,875,219 B2 | 4/2005 | Arramon et al. | |
| 7,008,433 B2 | 3/2006 | Voellmicke et al. | |
| 7,025,771 B2 | 4/2006 | Kuslich et al. | |
| 7,044,954 B2 * | 5/2006 | Reiley et al. | 606/93 |
| 7,097,648 B1 | 8/2006 | Globerman et al. | |
| 7,144,398 B2 * | 12/2006 | Chern Lin et al. | 606/92 |
| 7,175,629 B2 | 2/2007 | Lin et al. | |
| 7,226,481 B2 | 6/2007 | Kuslich et al. | |
| 7,250,055 B1 | 7/2007 | Vanderwalle | |
| 7,544,196 B2 * | 6/2009 | Bagga et al. | 606/93 |
| 7,621,950 B1 | 11/2009 | Globerman et al. | |
| 7,655,010 B2 | 2/2010 | Sehan | |
| 7,722,624 B2 * | 5/2010 | Boucher et al. | 606/105 |
| 7,799,035 B2 | 9/2010 | Krueger et al. | |
| 7,931,689 B2 * | 4/2011 | Hochschuler et al. | 623/17.12 |
| 8,147,500 B2 * | 4/2012 | Beyar et al. | 606/94 |
| 8,415,407 B2 | 4/2013 | Beyar et al. | |
| 2001/0039453 A1 | 11/2001 | Gresser et al. | |
| 2002/0058947 A1 | 5/2002 | Hochschuler | |
| 2003/0009225 A1 | 1/2003 | Khandkar et al. | |
| 2003/0028251 A1 | 2/2003 | Matthews | |
| 2004/0073213 A1 | 4/2004 | Serhan et al. | |
| 2004/0102774 A1 | 5/2004 | Trieu | |
| 2005/0070900 A1 | 3/2005 | Serhan et al. | |
| 2006/0079905 A1 | 4/2006 | Beyar et al. | |
| 2006/0264967 A1 | 11/2006 | Ferreyro et al. | |
| 2007/0032567 A1 | 2/2007 | Beyar et al. | |
| 2007/0055280 A1 | 3/2007 | Osorio et al. | |
| 2010/0023017 A1 | 1/2010 | Beyar et al. | |

FOREIGN PATENT DOCUMENTS

| | | |
|---|---|---|
| IL | 174347 | 3/2006 |
| WO | WO 97/37619 | 10/1997 |
| WO | WO 02/30338 | 4/2002 |
| WO | WO 02/062272 | 8/2002 |
| WO | WO 2006/090379 | 8/2006 |

OTHER PUBLICATIONS

Canadian Requisition, from CA Appl. No. 2,540,525, dated Sep. 14, 2010.

Cortek, Inc.: Product Line [online], 2001-2002, http://www.cortekinc.com/product.html.

European Examiner's Report, from EP Appl. No. 04785211.6 dated Feb. 15, 2008.

European Examiner's Report, from EP Appl. No. 04785211.6 dated Feb. 16, 2009.

FDA Approves Cambridge Scientific Inc's Orthopaedic WISORB Malleolar Screw, Cambridge MA Jul. 30, 2002 www.cambridgescientificinc.com, retrieved on Oct. 14, 2003.

Haas, N., New Products From AO Development [online], May 2002, http://www.ao.asitch/development/pdf_tk_news 02.pdf (retrieved Oct. 14, 2003).

International Preliminary Report on Patentability, from PCT/US04/031846.

International Search Report, from PCT/US04/031846, mailed Feb. 17, 2005.

International Search Report, from PCT/IL07/00484, mailed Apr. 23, 2009.

Kandziora, F et al., "Biomechanical Analysis of Biodegradable Interbody Fusion Cages Augmented With Poly(Propylene Glycol-co-Fumaric Acid)," SPINE 27(15):1644-51 (2002).

OSTEOSET DBM Pellets (Important Medical Information)[online], Nov. 2002, http://www.wmt.com/Lierature, retrieved on Oct. 14, 2003.

Supplementary European Search Report, from EP Appl. No. 07736224.2, dated Nov. 19, 2010.

* cited by examiner

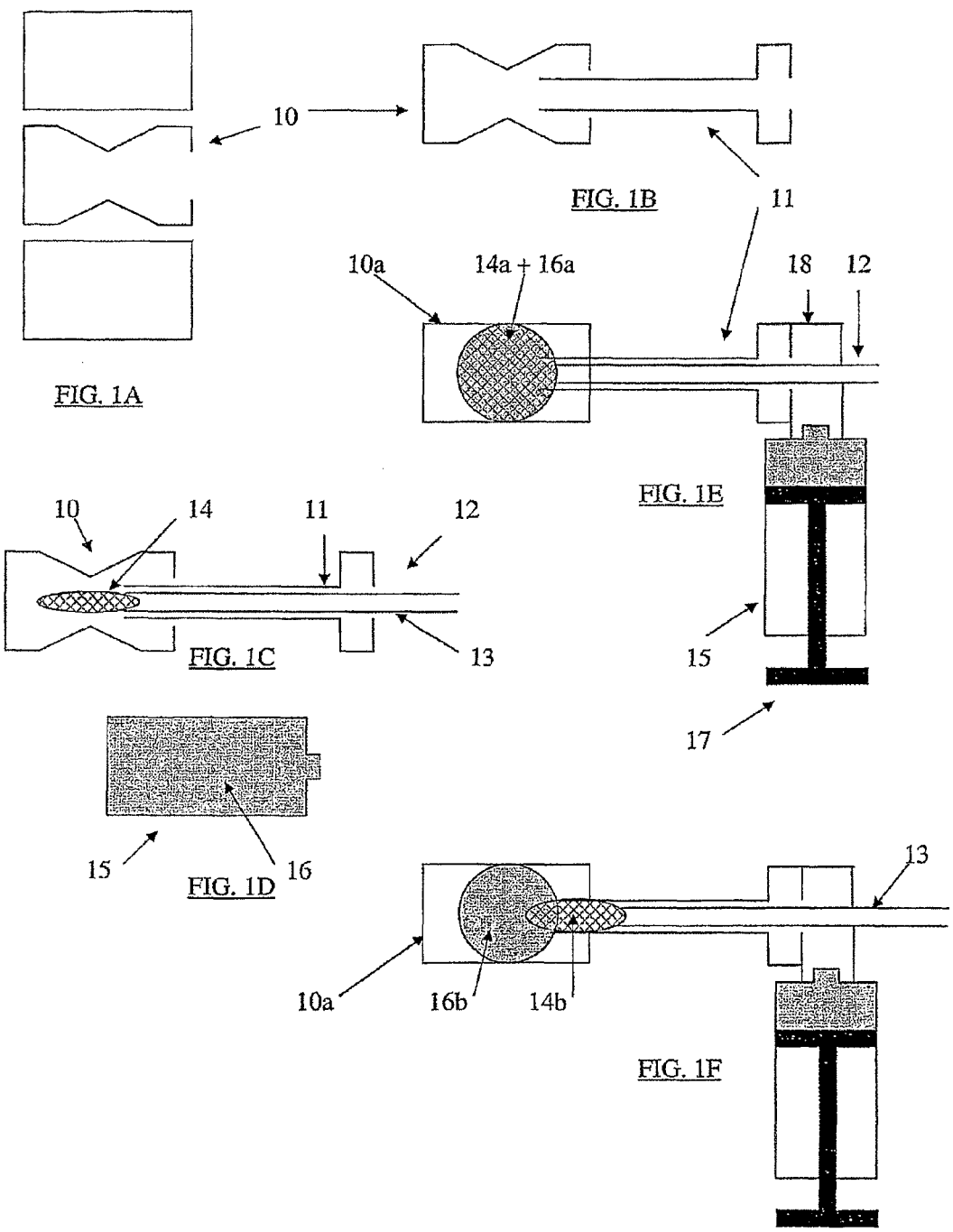

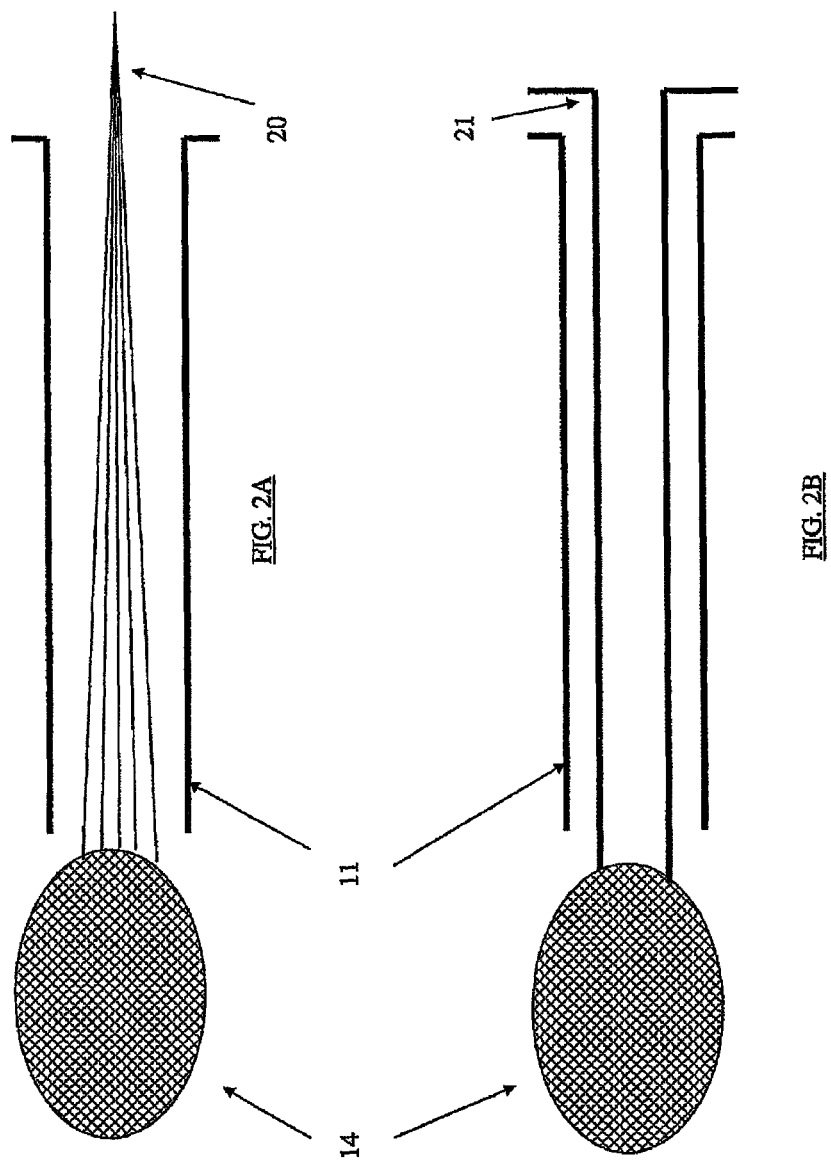

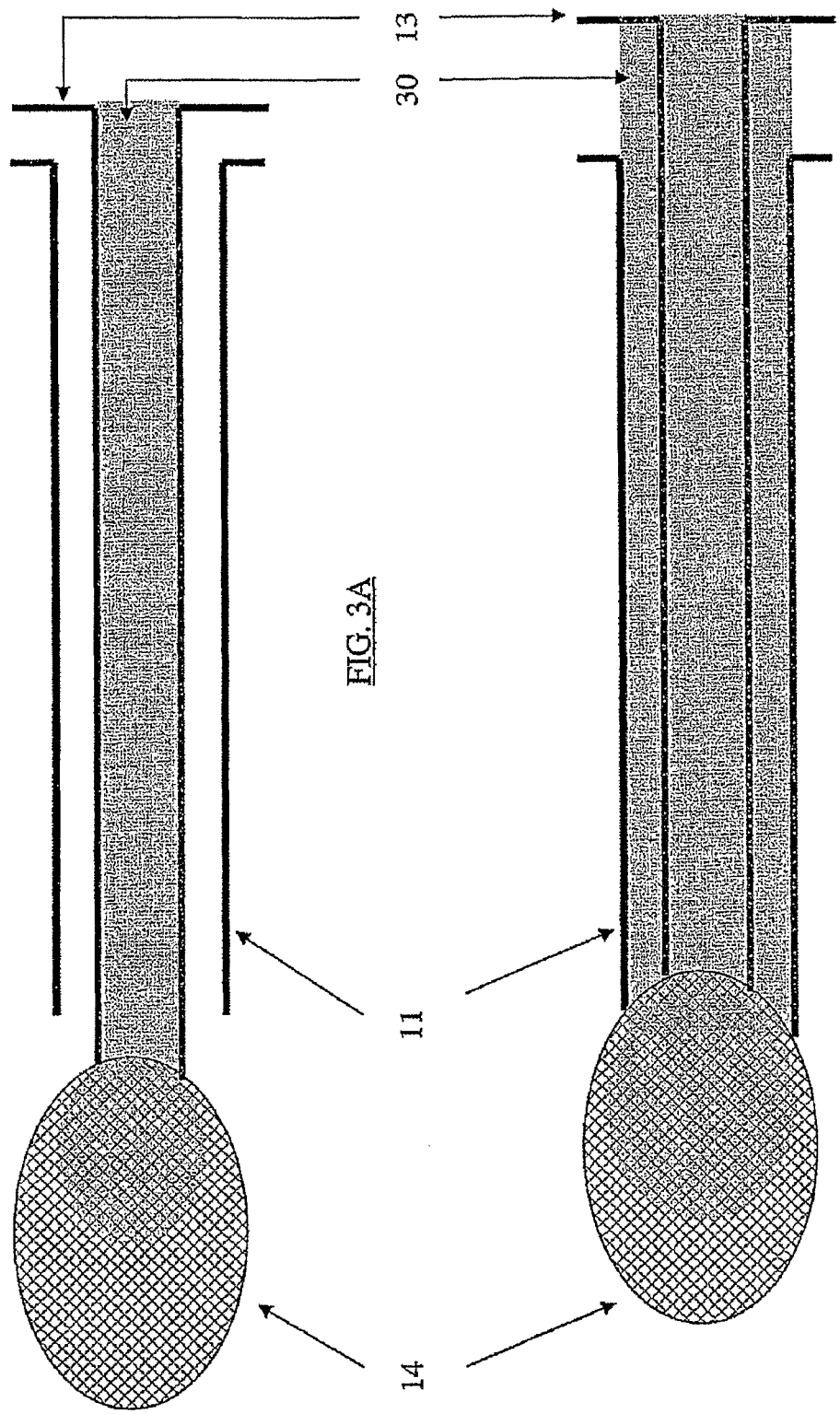

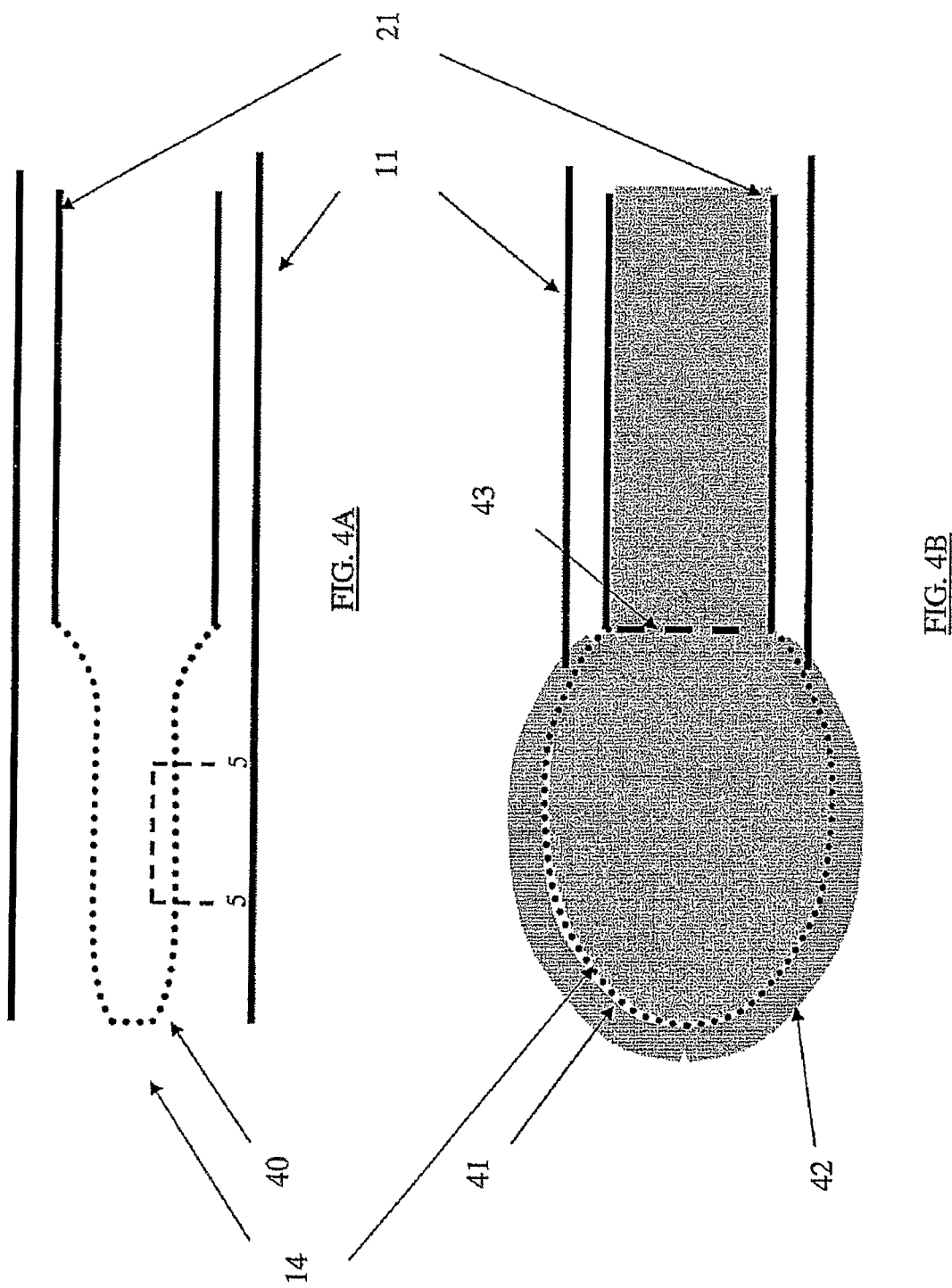

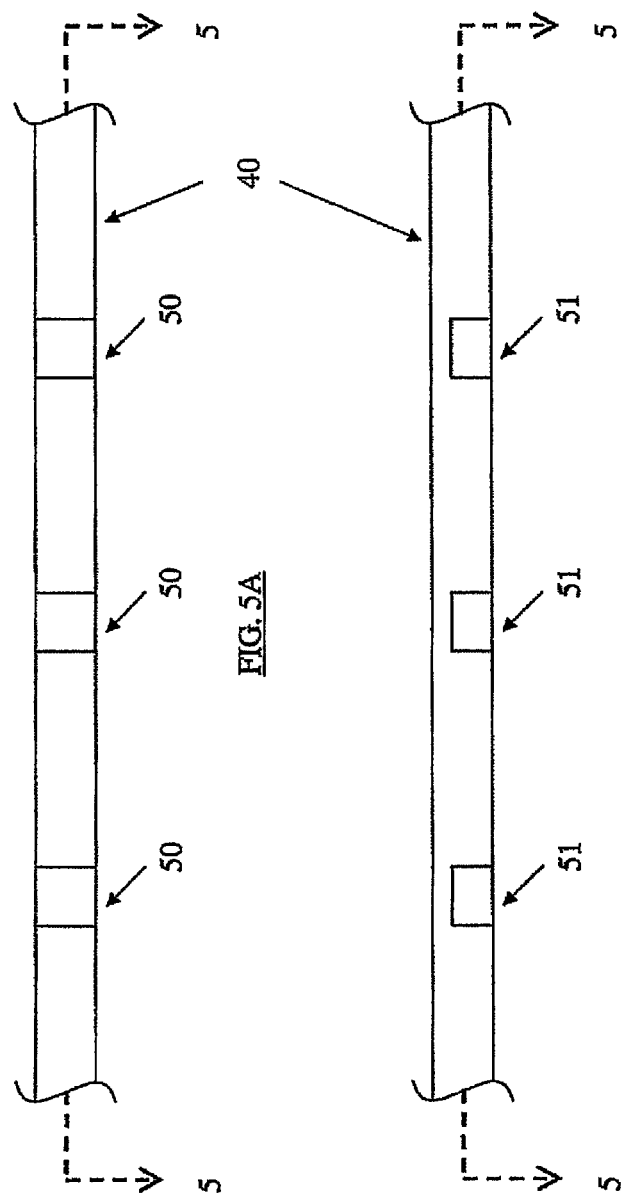

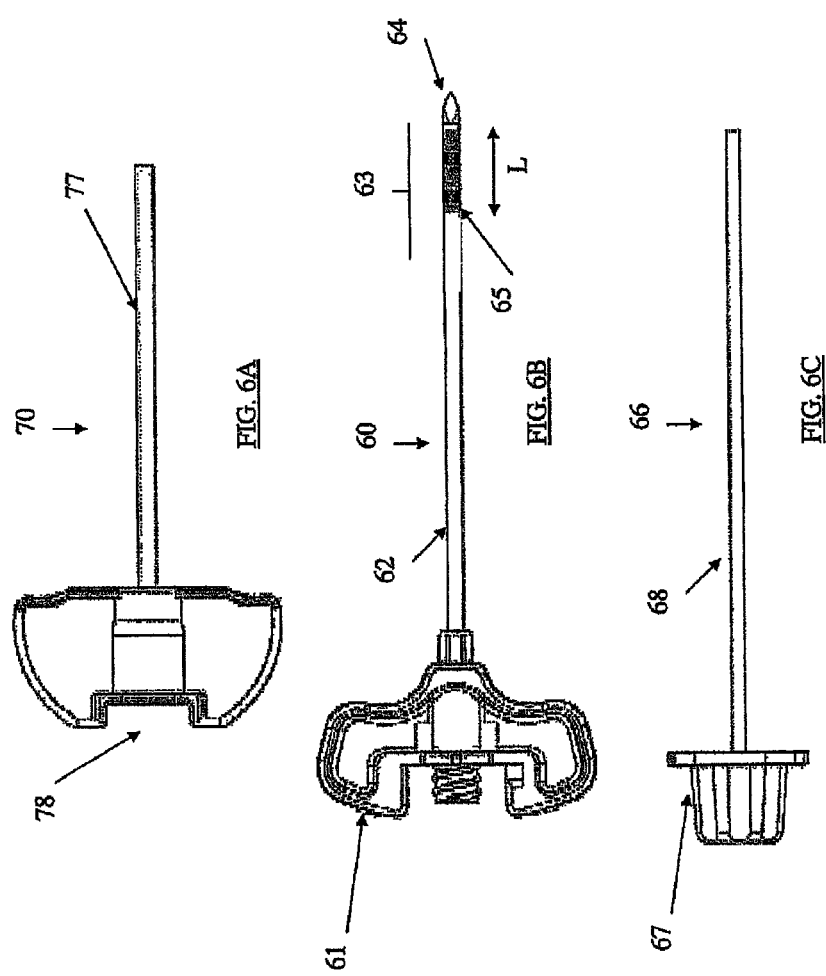

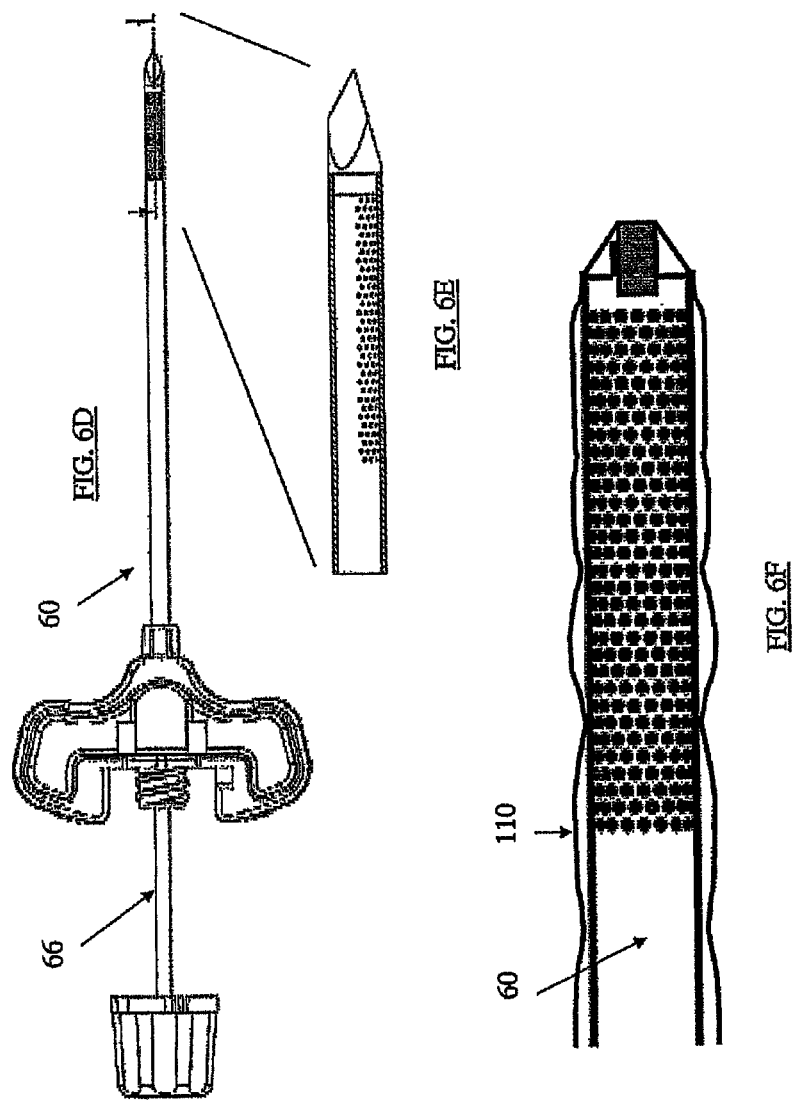

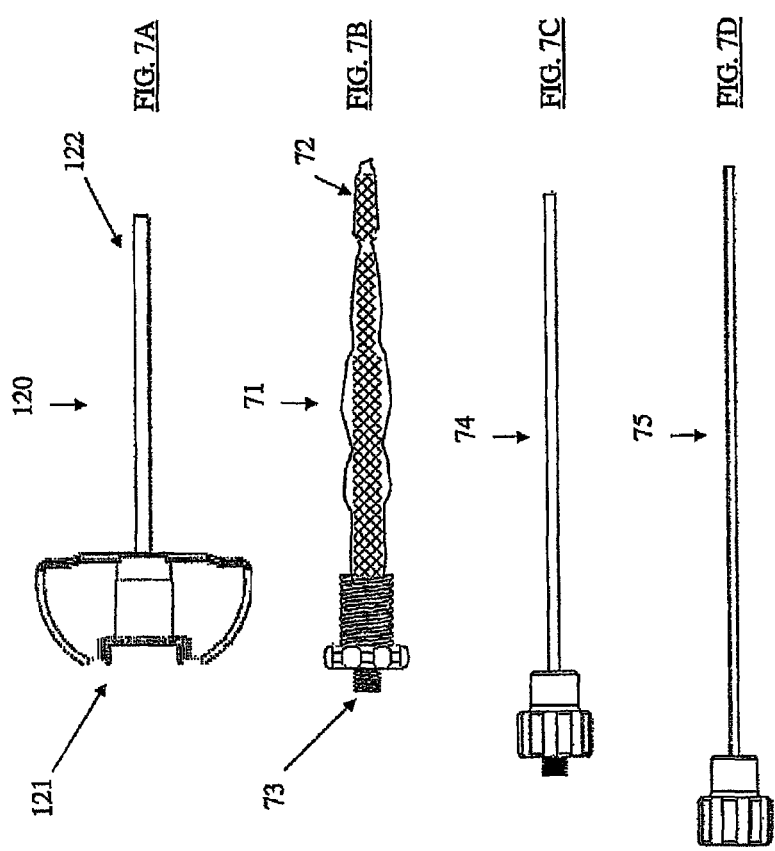

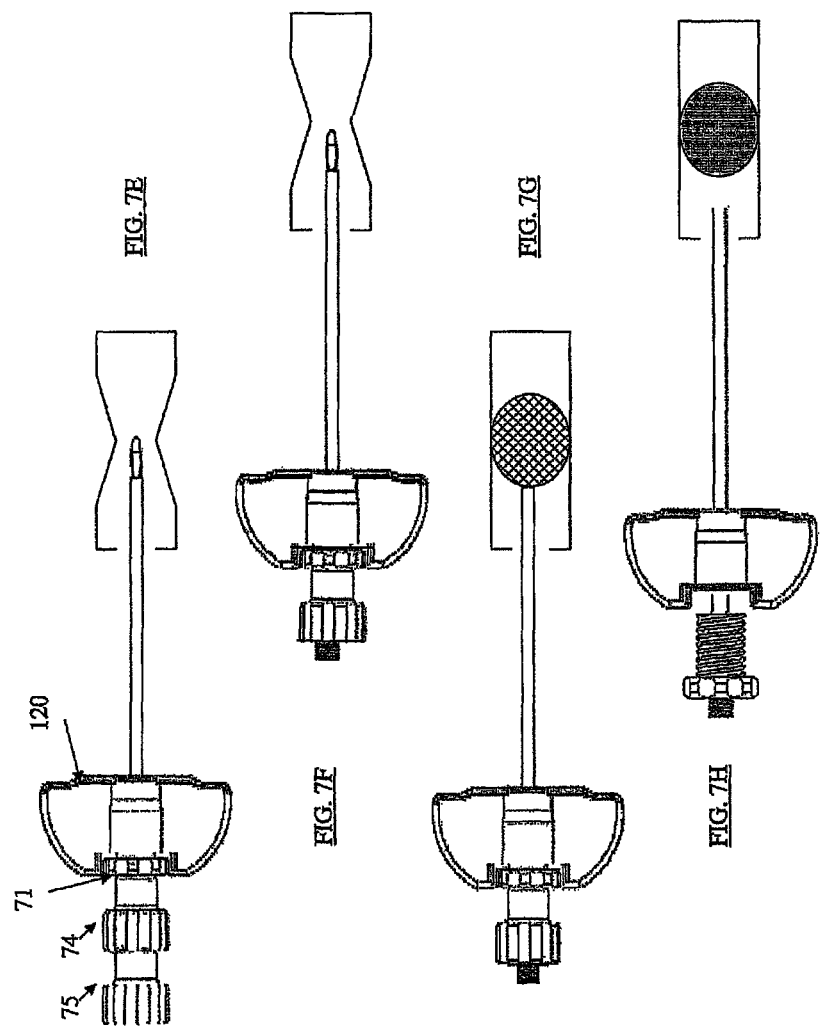

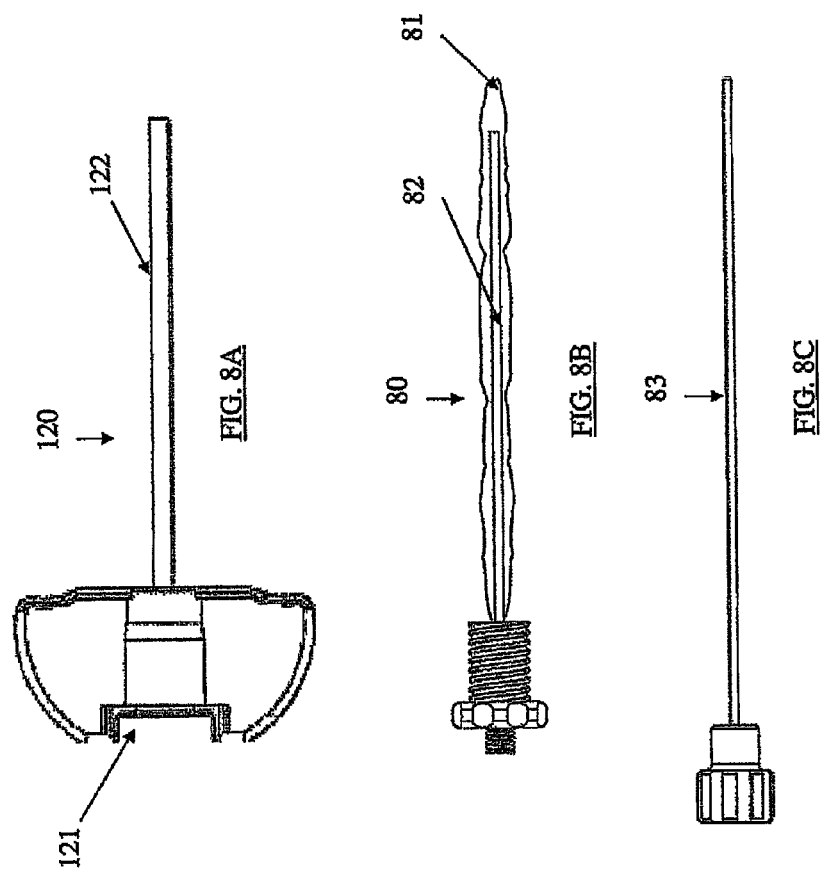

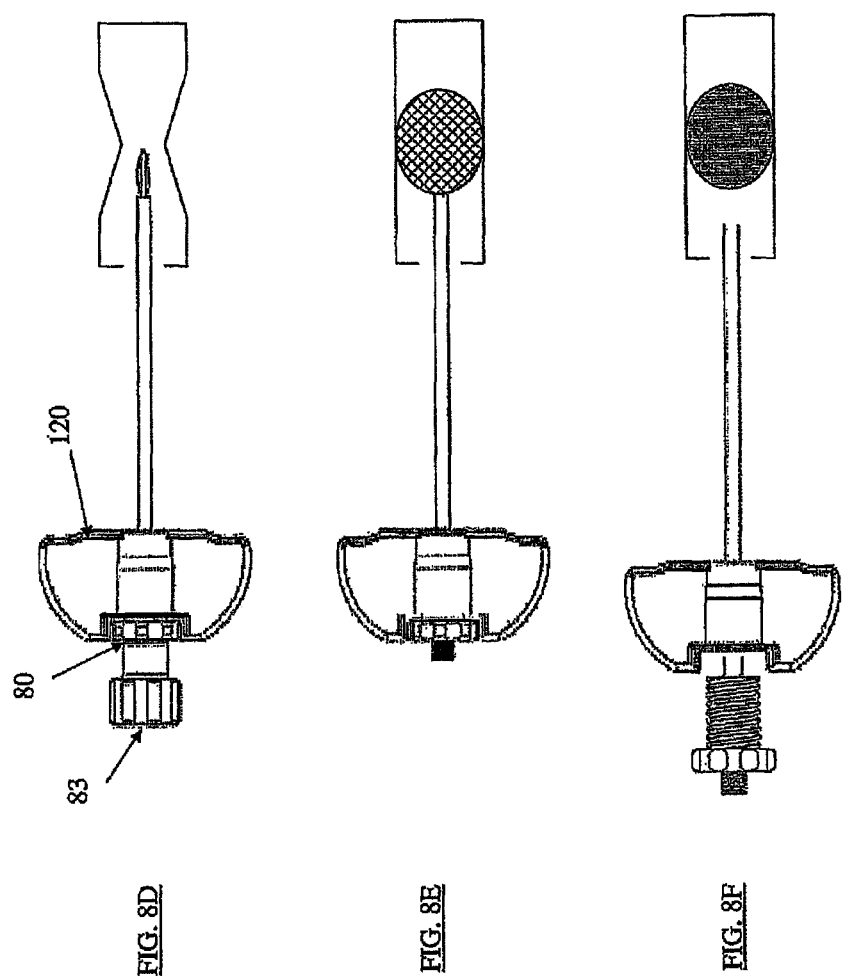

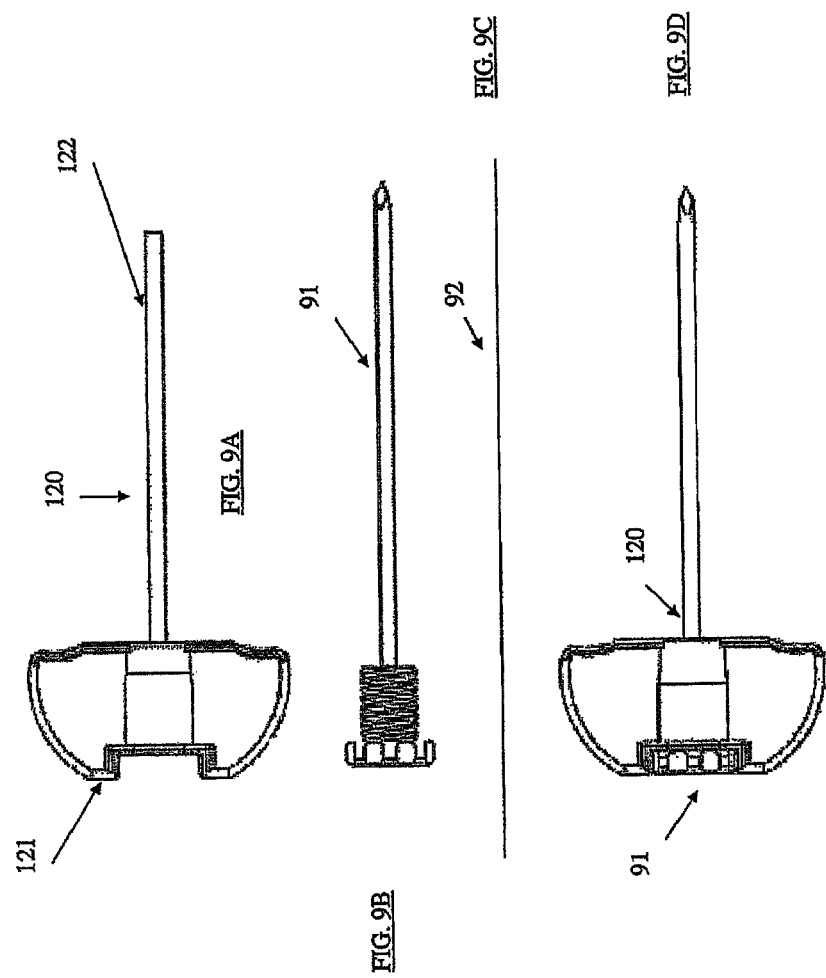

INSTRUMENTATION KIT FOR DELIVERING VISCOUS BONE FILLER MATERIAL

CROSS REFERENCE TO RELATED APPLICATIONS

The present application is a continuation of U.S. application Ser. No. 12/296,538, filed Sep. 10, 2009, which is a U.S. National Phase Application of PCT/IL07/000484, filed Apr. 17, 2007, which is related to U.S. provisional application 60/793,259 filed on Apr. 20, 2006 and entitled "Expandable-Collapsible Permeable Delivery System for VCF Correction and Method of Use", to U.S. provisional application 60/825,609 filed on Sep. 14, 2006 and entitled "Bone Cement and Methods of Use Thereof", and to U.S. patent application Ser. No. 11/461,072 filed on Jul. 31, 2006 and entitled "Bone Cement and Methods of Use Thereof", which is a Continuation-in-Part of U.S. application Ser. No. 11/360,251 filed on Feb. 22, 2006, entitled "Methods, Materials and Apparatus for Treating Bone and Other Tissue" and is also a Continuation-in Part of PCT/IL2005/000812 filed on Jul. 31, 2005. The disclosures of these applications are incorporated herein by reference.

The present application is also related to PCT application PCT/IL2006/052612 filed on Jul. 31, 2006 and entitled "Bone Cement and Methods of Use thereof" the disclosure of which is incorporated herein by reference, to Israel application No. 174347 filed on Mar. 16, 2006 and entitled "Bone Cement and Methods of Use thereof" the disclosure of which is incorporated herein by reference, and to a series of US provisional applications entitled "Methods, Materials and Apparatus for Treating Bone and Other Tissue": 60/765,484 filed on Feb. 2, 2006; 60/762,789 filed on Jan. 26, 2006; 60/738,556 filed Nov. 22, 2005; 60/729,505 filed Oct. 25, 2005; 60/720,725 filed on Sep. 28, 2005 and 60/721,094 filed on Sep. 28, 2005. The disclosures of these applications are incorporated herein by reference.

The present application is also related to PCT application PCT/IL2006/000239 filed on Feb. 22, 2006; U.S. provisional application 60/763,003, entitled "Cannula" filed on Jan. 26, 2006; U.S. provisional application No. 60/654,495 entitled "Materials, devices and methods for treating bones". filed Feb. 22, 2005; U.S. Ser. No. 11/194,411 filed Aug. 1, 2005; IL 166017 filed Dec. 28, 2004; IL 160987 filed Mar. 21, 2004; U.S. Provisional Application No. 60/654,784 filed on Jan. 31, 2005; U.S. Provisional Application No. 60/592,149 filed on Jul. 30, 2004; PCT Application No. PCT/IL2004/000527 filed on Jun. 17, 2004, Israel Application No. 160987 filed on Mar. 21, 2004, U.S. Provisional Application Nos. 60/478,841 filed on Jun. 17, 2003; 60/529,612 filed on Dec. 16, 2003; 60/534,377 filed on Jan. 6, 2004 and 60/554,558 filed on Mar. 18, 2004; U.S. application Ser. No. 09/890,172 filed on Jul. 25, 2001; U.S. application Ser. No. 09/890,318 filed on Jul. 25, 2001 and U.S. application Ser. No. 10/549,409 entitled "Hydraulic Device for the injection of Bone Cement in Percutaneous Vertebroplasty filed on Sep. 14, 2005. The disclosures of all of these applications are incorporated herein by reference.

BACKGROUND OF THE INVENTION

1. Field of the Invention

The present invention relates to devices and methods for injection of a viscous material into a living subject. This invention particularly relates to devices and methods for filling bone voids. This invention more particularly relates to height restoration of a bone, for example, for treating Vertebral Compression Fractures (VCFs).

2. Description of the Related Art

A common occurrence in older persons is compression fractures of the vertebrae. This causes pain and a shortening (or other distortion) of stature. One common treatment is vertebroplasty, in which cement is injected into a fractured vertebra. While this treatment fixes the fracture and reduces pain, it does not restore the vertebra and person to their original height. Another problem with vertebroplasty, is that because the cement is injected as a liquid, it may leak outside of the vertebra, for example, through cracks in the vertebra. This may cause considerable bodily harm.

Viscous cement may reduce the risk of leakage, while sustaining an ability to infiltrate into the intravertebral cancellous bone (interdigitation) [see G Baroud et al, Injection biomechanics of bone cements used in vertebroplasty, Bio-Medical Materials and Engineering 00 (2004) 1-18]. In addition, viscous material may reduce the fracture. For example, PCT Application No. PCT/IL2006/000239 and IL Patent Application No. 174347 to Beyar et al. describe bone cements with certain formulations, commercially known as Confidence Bone Cement™, which provide an enhanced high-viscosity window of time during which the cement is suitably viscous for injection, fit using a designated delivery system and which are incorporated by reference herein. This type of bone cement rapidly achieves a high viscosity when its components are mixed and set slowly. The liquid phase is skipped during and immediately following the mixing of the components.

Another common treatment for fractured vertebras is kyphoplasty. This was first described in U.S. Pat. Nos. 5,108,404 and 4,969,888 to Scholten et al., wherein a fracture of a vertebra is taught to be reduced by first inflating a balloon inside the vertebra and thereby producing compaction of the cancellous bone to form a cavity. Bone cement is subsequently injected into the cavity after the balloon is withdrawn. The cement fills the cavity. In this procedure, because a lower pressure can be used to inject the cement, the problem of cement migration is reduced. However, this problem is not completely avoided.

U.S. Pat. Nos. 5,549,679 and 5,571,189 to Kuslich describe a device and method for stabilizing a spinal segment with an expandable, porous fabric implant for insertion into the interior of a reamed out disc which is packed with material to facilitate body fusion. U.S. application Ser. No. 10/440,036 of Kuslich et al. describes an improved method of correcting bone abnormalities by first accessing and boring into the damaged tissue or bone, and then reaming out the damaged and/or diseased area. Alternatively, the cancellous bone may be compacted by expanding a bag within the damaged bone. The bag may then be filled with fill material, such as a bone repair medium, thereby correcting and stabilizing the bony defect and deformity in a single step. This type of bag may be inflated with less fear of puncture and leakage of the inflation medium than a thin walled rubber balloon. Furthermore, this procedure provides the advantage of safely skipping the first balloon inflation steps of Scholten, by expanding the bag by introducing fill material, such as a bone repair medium and thereby correcting and stabilizing the bony defect and deformity in a single step. Nevertheless, this procedure is accomplished only by leaving the expanded bag inside the body organ after the injected material has solidified. Furthermore, when the bag is filled with inert filling materials, it is intentionally designed not to allow said material transfer through bag walls.

U.S. patent application Ser. No. 10/949,217 to Lin et al. describes an extractable device for inserting a medicinal filling into a vertebral body. In this procedure, a filling member is made of a flexible and permeable wall. After the filling member is inserted into the spinal disc and/or vertebra, and a flowable medicine is injected and fully solidifies therein, closing threads are pulled to unlash the opening of a holding portion provided with the filling member. This enables the filling member to be extracted from the spinal disc to leave only the medicine in the spinal disc. Lin et al. do not describe a method or a device, specifically intended for compacting cancellous bone and/or promoting height restoration of the vertebral body. Further, Lin et al. discloses threads located on the distal end of the bag which are not for connecting the bag to other means.

It is the object of this invention to provide an improved method and apparatus that for treating a fractured vertebral body, and significantly lowering the risk of filler material leakage.

SUMMARY OF THE INVENTION

The present invention provides method and device by which a bone void filler is introduced into a fractured bone (e.g., vertebral body), while the risk of leakage is minimized. An aspect of some embodiments of the invention relates to a device for filling a void in a patient's bone with bone void filler. The device comprises a mechanism having a permeable element secured without releasable threads thereto and a cannula for extending into the bone and for guiding said mechanism to the void. When the permeable element is in a collapsed state it may pass through the cannula and then expand within the bone when the bone void filler is applied under pressure thereto.

Another aspect of some embodiments of the invention includes that the permeable element is permeable to the bone void filler so that the bone void filler may flow into the void when pressure is applied thereto.

Some embodiments of the invention may include an injection needle for extending into the permeable element for injecting the bone void filler therein.

Other embodiments of the invention may also include a pressurizing device for delivering the bone void filler into the permeable element.

A further aspect of some embodiments of the invention relates to a device for delivering bone filler material to a bone void comprising a longitudinal channel having a proximal end and a distal end. The channel has a perforated segment and the distal end is sealed so that the bone filler material may be applied to the bone void through the perforated segment.

Some embodiments of the invention may include that the perforated segment is on the channel wall proximate the distal end.

Other embodiments of the invention may include that the perforated segment is circumferentially around a portion of said channel wall.

A still further aspect of some embodiments of the invention relates to a method of introducing bone void filler into a void in a patient's bone. The method comprises inserting a cannula into the bone, inserting a collapsed permeable element through the cannula into the bone, expanding the permeable element with bone void filler, and then extruding the bone void filler into the bone void by extracting the permeable element through the cannula.

Another method of an embodiment of the present invention includes introducing bone void filler into a void in a patient's bone by inserting a cannula into the bone, inserting a mechanism having a collapsed permeable element through the cannula into the bone, wherein the permeable element is secured to the mechanism without threads, applying the bone void filler into the bone through the permeable element, and then extracting the permeable element through the cannula. Additional objects of the present invention will become apparent from the following description.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein:

FIGS. 1A-1F are diagrammatic representations of an embodiment of the method of the present invention.

FIGS. 2A and 2B are diagrammatic representations of embodiments of extraction mechanisms of the present invention.

FIGS. 3A and 3B are diagrammatic representations of embodiments of delivery methods and devices of material of the present invention.

FIG. 4A is a diagrammatic representation of an embodiment of a collapsed formation of a permeable walled structure of the present invention.

FIG. 4B is a diagrammatic representation of an embodiment of an expanded formation of a permeable walled structure of the present invention.

FIGS. 5A and 5B are diagrammatic representations of longitudinal sectional views of embodiments of permeable elements walls of the present invention.

FIG. 6A illustrates an embodiment of a guiding cannula for VCF treatment.

FIG. 6B illustrates an embodiment of a fenestrated cannula for VCF treatment.

FIG. 6C illustrates an embodiment of an inner rod of the guiding cannula of the present invention.

FIG. 6D illustrates the inner rod partially inserted into the guiding cannula of the present invention.

FIG. 6E illustrates an enlarged view of the distal end of the fenestrated cannula of the present invention.

FIG. 6F illustrates an embodiment of the fenestrated cannula covered with meshed sleeve.

FIG. 7A illustrates another embodiment of a guiding cannula for VCF treatment.

FIG. 7B illustrates an embodiment of a longitudinal sleeve of the present invention.

FIG. 7C illustrates an embodiment of an injection needle of the present invention.

FIG. 7D illustrates another embodiment of an inner rod (a stylet) of the present invention.

FIG. 7E illustrates an embodiment of an assembled cannula inserted into a vertebra for VCF treatment.

FIG. 7F illustrates withdrawing the stylet from the vertebra.

FIG. 7G illustrates expanding the sleeve by pressurizing the bone filler material into the injection needle in an embodiment for VCF treatment.

FIG. 7H illustrates withdrawing the sleeve out of the body while extracting at least part of the remaining bone filler material through the meshed walls.

FIG. 8A illustrates another embodiment of a guiding cannula for VCF treatment.

FIG. 8B illustrates another embodiment of a longitudinal sleeve of the present invention.

FIG. 8C illustrates another embodiment of a stylet of the present invention.

FIG. 8D illustrates another embodiment of an assembled cannula inserted into a vertebra for VCF treatment.

FIG. 8E illustrates expanding the sleeve by pressurizing the bone filler material into the injection needle in the embodiment illustrated in FIG. 8A.

FIG. 8F illustrates withdrawing the sleeve out of the body in the embodiment illustrated in FIG. 8A.

FIG. 9A illustrates another embodiment of a guiding cannula for VCF treatment.

FIG. 9B illustrates a drill for use in the embodiment illustrated in FIG. 9A.

FIG. 9C illustrates a guide wire for use in the embodiment illustrated in FIG. 9A.

FIG. 9D illustrates another assembled bone drilling/accessing tool for VCF treatment.

DETAILED DESCRIPTION OF EXEMPLARY EMBODIMENTS

Figure 10B:
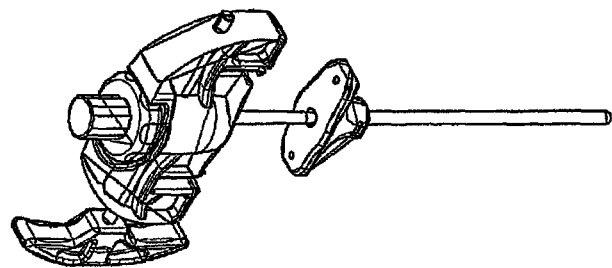
FIG. 10B is an isometric view of the embodiment shown in FIG. 10A.

The following exemplary embodiments as exemplified by the drawings are illustrative of the invention and are not intended to limit the invention as encompassed by the claims of this application. An apparatus and method for filling bone voids is disclosed herein.

General Exemplary Procedure

FIGS. 1A-F generally illustrate a method for filling bone voids. Such voids may often be a result of a compression fracture and may be treated in accordance with such an exemplary embodiment of the invention. X-ray or CT images are usually used for identifying a bone fracture. For example a vertebra or other bone may be damaged or fractured by a compression fracture. Alternatively, a vertebra may be fractured because of weakening caused by osteoporosis or by other pathological conditions. FIG. 1A shows a schematic lateral view of a vertebral body 10 having compression fracture. Although following descriptions focus upon vertebral compression fractures, some embodiments of the invention are not limited to treatments due solely to such cases.

In an exemplary embodiment of the invention, access may be is minimally invasive. For example, only a single channel may be formed into the body. FIG. 1B shows a guiding cannula 11 inserted into a body, for example, within a fractured vertebral body 10. The procedure described herein may use a cannula having a diameter ranging from about 5 mm to about 0.5 mm. For example, a cannula may have a diameter of about 5 mm, about 4 mm, or less in diameter. In some cases, multiple openings into the body may be formed. This procedure may alternatively use a surgical or key-hole incision. However, a surgical or key-hole incision may require a longer recuperation period by the patient. In other embodiments, the cannula (and the corresponding length of a delivery tube described below) may range from about 50 mm to about 100 mm. For example the cannula may be about 50 mm, about 70 mm, about 100 mm, or more, or intermediate, or smaller values.

FIG. 1C shows a mesh structure 12, comprising an expandable-collapsible permeable element 14 and an extraction mechanism 13. These elements are introduced into guiding cannula 11. The permeable element 14 is placed in a optionally preferred location, as chosen by the physician. The permeable element 14 is attached to the distal side of the extraction mechanism 13 and is introduced and placed in the body in a collapsed configuration.

A predetermined amount of bone void filler 16 is prepared. As illustrated in FIG. 1D, a filler material reservoir 15 is then filled with the prepared bone void filler. The prepared bone void filler material 16 may be prepared for setting into a hardened condition, for example, as in the case of setting bone cement. Alternatively, the prepared bone filler material may be a non-hardening material.

In one embodiment of the invention, the bone cement may have an enhanced high-viscosity window before it sets. Its viscosity, although relatively high, may not vary to a degree that adversely affects injection parameters. Alternatively, the viscosity in the window may be about 500, or about 1,000, or about 1,500, or about 2,000 Pascal-sec, or less, or more, or of an intermediate value. In another embodiment of the invention, the working window may be at least about 3 minutes, or at least about 5 minutes, or at least about 8 minutes, or at least about 10 minutes, or at least about 15 minutes, or at least about 20 minutes. The increased viscosity may alternatively provide a short time after mixing of the cement components, for example, zero time (for a pre-provided viscous material). Alternatively, it may be less than about 1 minutes, or less than about 2, or less than about 3 minutes after mixing is complete. Alternative examples of setting and non-setting bone cements are thoroughly described in PCT application No. PCT/IL2006/000239 and IL patent application No. 174347 to Beyar et al., the disclosures of which are fully incorporated herein by reference.

In one embodiment of the invention, the permeable element has at least one flexible segment.

In another embodiment of the invention, at least part of the permeable element is a fabric material, whereas said fabric can be woven or non-woven, knitted, braided, molded or be constructed in any other method known in the art. In yet another exemplary embodiment of the invention, at least part of the permeable element is made of a biocompatible material, such as stainless steel, rubber, elastic plastic, synthetic fiber, PMMA, titanium, goat intestine, and the like. Optionally, the permeable element can be formed into an object in the form of sac, bag, cylinder, rectangular column, sphere, torus, kidney-bean configuration, pyramid, cylindrical ellipse, or any combination of such configurations, integrally or by joining separate pieces. In an exemplary embodiment of the invention, the permeable element may contain a ray imaging material, such as a metal wire, by which the precise position of the filling member can be easily located by a ray imaging system, such as an X-ray machine. In embodiment of the invention, the flexible segment and/or fabric material may be of a one-layered or multi-layered construction, depending on the particle size and/or the viscosity of the bone void filler.

As shown in FIG. 1E, the filler material reservoir is then connected on its distal side to the guided cannula and/or to a mesh structure 12. The connection may be accomplished either with or without a special adapter 18. The proximal side of the material reservoir may be coupled to an optionally preferred pressurizing device. This pressuring device, capable of injecting the bone void is schematically illustrated as plunger 17. When the plunger is actuated, pressure therein increases sufficient for forcing a quantity of bone void filler 16a into the permeable element. The bone void filler flows thereto until the permeable element expands to an optionally preferred expanded formation 14a.

In one embodiment of the invention, the proximal opening of the guiding cannula or the extraction mechanism may be attached to a syringe and/or to any other bone cement delivery system known in the art. In another embodiment of the invention, the injection port of the guiding cannula or the extraction mechanism may be attached to a distal end of a bone filler reservoir. The reservoir may be alternatively attached to a pressurizing hydraulic system on its proximal side. In another embodiment of the invention, the system may be manually operable, and/or by foot, and/or by battery power. In a further embodiment of the invention, the pressurizing system may provide sufficient pressure to deliver at least about 5 ml, or at least about 10 ml of viscous bone cement as a single continuous aliquot. In a still further embodiment of the invention, the pressure source may provide a pressure of about 50, or about 100, or about 150, or about 200, or about 300 atmospheres, or less, or more, or of and intermediate value. In another embodiment of the invention, the system design may assure that the physician's hands are located outside an X-ray radiation zone. In another embodiment of the invention, an actuator for a pressure source may be located about 20 cm, about 40 cm, about 60 cm, about 100 cm, or an intermediate or greater distance from a cement reservoir. Examples of hydraulic delivery devices are thoroughly described in PCT application No. PCT/IL2006/000239 and IL patent application No. 174347 to Beyar et al., the disclosures of which are fully incorporated herein by reference.

The expansion of the permeable element preferably restores at least part of the height of the vertebra to its former height. The expansion may restore, for example, up to about 20%, about 40%, about 60%, about 80%, or intermediate, or higher percentages of a pre-compression height. A particular feature of some embodiments of the invention is that the provided material is of sufficient viscosity or sufficiently solidity for preventing or reducing leakage from the permeable element until the optionally preferred expansion is accomplished, especially as compared with leakage when using liquid PMMA cement. The pressure needed to inject the material may be higher than what is typically used in the art to accommodate the increased viscosity.

In another embodiment of the invention, the permeable element comprises at least one rigid segment. The permeable element may comprise any number of several rigid segments each capable of changing their formation with respect to one another. This may allow the permeable element to expand or collapse under certain preferred circumstances. In another embodiment of the invention, the rigid segments may be set as an expandable telescopic tube. In still another embodiment of the invention, the permeable element may comprise of at least one rigid element, elastic or inelastic, capable of stretching, elongating or changing its dimensions in any other way when inner-pressure applied changes. In a further embodiment of the invention, the rigid element may be made of shape memory material, such as Nitinol.

FIG. 1F illustrates extraction of the permeable element out of a vertebral body. This extraction is accomplished by the extraction mechanism 13. The removal of the permeable element forces it to re-collapse. The collapsing of the permeable element thereby forces the bone void filler material to penetrate and/or flow through the permeable element walls into the vertebral body until collapsing formation 14b occurs. To maintain adequate inner-pressure, a sufficient force upon on plunger may be applied. In an alternative method, the amount of filler material that flows through the permeable element walls may form a bulk material 16b. The location and/or the volume of the bulk material may be similar to that previously occupied by the permeable element in its expanded formation 16a. Preferably, the bulk material has the properties required for repairing fractures and preserving the height restoration that was achieved by the previous expansion of permeable element 14. The tube is removed after the procedure is completed.

Basic Extraction Mechanisms

FIGS. 2A and 2B illustrate basic extraction mechanisms in accordance with exemplary embodiments of the invention. FIG. 2A is a cross-sectional view of a mesh structure introducing system, generally comprising an expandable-collapsible permeable element 14 and an extraction mechanism 20 inside the guiding cannula 11. As schematically illustrated, the extraction mechanism may comprise several tension wires distally connected to permeable element 14. Alternatively, the wires may be elongated ends of threads fabricated into the permeable element walls.

FIG. 2B is a cross-sectional view of a mesh structure introducing system, generally comprising an expandable-collapsible permeable element 14 and an extraction mechanism 21 inside the guiding cannula. As schematically illustrated, the extraction mechanism may comprise an elongated body with outside dimensions sufficient for allowing introduction into the guiding cannula. Alternatively, the elongated body may be tubular, or hollow, or with slotted areas on its peripheral wall, or any combination thereof.

Basic Filler Material Delivery Devices and Methods

FIGS. 3A and 3B illustrate basic delivery methods and devices in accordance with exemplary embodiments of the invention. FIG. 3A is a cross-sectional view of a mesh structure introducing system, generally comprising an expandable-collapsible permeable element 14 and an extraction mechanism 13 inside the guiding cannula. As schematically illustrated, the bone void filler 30 may be delivered to the permeable element directly through the extraction mechanism. The permeable element may comprise a permeable or a leak proof hollow body. FIG. 3B illustrates a similar apparatus. In this embodiment, the guiding cannula serves as the delivery device of the bone void filler material. The bone void filler material may flow the through location occupied by the extraction mechanism within the guiding cannula, or it may flow in the space created therebetween, depending upon the specific configuration of the extraction mechanism (including the example described with respect to FIGS. 2A-B).

Basic Permeable Walled Structures

FIGS. 4A and 4B show a collapsed formation and an expanded formation of permeable walled structure, respectively, in accordance with exemplary embodiments of the invention. FIG. 4A is a cross-sectional view of an expandable-collapsible permeable element 14 attached to extraction mechanism 21 inside the guiding cannula. The permeable element is shown in its first alternatively preferred collapsed formation 40. The permeable element can be positioned inside the guiding cannula either in whole or in part when collapsed until it is placed in the vertebral body prior to the injection of the filler material.

Dotted line 5-5 shows a section of the permeable element. As shown in FIGS. 5A and 5B, the permeable element wall may contain several through holes 50 or "blind" holes 51. These holes permit flow or extrusion of bone void filler material into cancellous bone and/or into a cavity formed in the vertebral body. In an exemplary embodiment of the invention, the diameter of the holes may range from about 0.1 mm to about 0.5 mm. Alternatively, the flow or extrusion from the holes may occur only after the permeable element has expanded to its preferred formation configuration. Preferably, the flow or extrusion may occur only during extraction of the permeable element out of the vertebral body into the distal opening of the cannula.

The blind hole or holes of the permeable element are preferably closed and may be capable of being burst by the bone void filler when a higher inner-pressure is achieved and after the permeable element has expanded to a preferred size or configuration. Alternatively, the hole(s) of the permeable element may be open and have certain diameter or size, which permits flowing or exudation of the filler material with certain properties and only after a preferable inner-pressure is met. The diameter and size of the holes may vary. Alternatively, a hole's diameter and/or shape may be changed before, during, or after expansion and/or injection of bone void filler.

Preferably, the inner-pressure of the permeable element may be developed when or after the permeable element has expanded to a preferred size or configuration and is extracted from the vertebral body. The diameter of the holes may range from about 0.1 mm to about 0.5 mm. The inner-pressures may exceed 20 to 300 Atmospheres. In one embodiment of the invention, the holes may be located in specific areas of the permeable element thereby permitting a flowing of bone void filler to a specific location in vertebral body and/or in a specific flowing direction.

FIG. 4B illustrates another configuration of the permeable element after it has expanded to another preferred expanded formation 41. As schematically illustrated, the bone void filler material has filled the volume enclosed by the permeable element and is shown as it emerges through the holes. Preferably, the bone filler material is delivered to the permeable element through an opening port 43.

Example 1

Using a Perforated Cannula

FIGS. 6A-6E show an exemplary set of instruments that can be used for VCF treatment. The embodiments of the set comprises a guiding cannula 70 (shown in FIG. 6A), a fenestrated cannula 60 (shown in FIG. 6B), and an inner rod/stylet 66 (shown in FIG. 6C). The cannula 60 and the inner rod 66 may be assembled (as shown in FIG. 6D) prior to insertion into the body. Generally, the inner rod 66 may be used, when a further hardening of the cannula is needed (e.g., improved bending durability) during insertion into the bone. The guiding cannula 70 generally comprises a handle 77 and a body 78 and may be made of any rigid biocompatible material (e.g. stainless steel).

The cannula 60 comprises a handle 61 and a body 62 having a distal end 63. The cannula 60 may be made of any rigid biocompatible material (e.g. stainless steel). Preferably, the cannula body 78 may be made long enough to reach the inner volume of a vertebra during posterior and/or anterior surgeries. A perforated area with plurality of pores 65 may be placed along at least part of the cannula distal end 63. Alternatively, there may be at least 2 pores, or at least 10 pores, or at least 50 pores, or at least 100 pores, or at least 200 pores, or at least 500 pores. In one exemplary embodiment of the invention, the area of the pores has a length L of about 1 mm, or about 10 mm, or about 20 mm, or about 40 mm or lesser, or greater, or of intermediate values. Alternatively, the area of the pores may cover a full rotation around the longitudinal axis of the cannula 60 (not shown). Alternatively, the area of the pores may cover less than a full rotation around the same longitudinal axis (as shown in FIG. 6E). In one exemplary embodiment of the invention, the diameter of each pore may be about 0.1 mm, or about 0.3 mm, or about 0.5 mm, or lesser, or greater, or of intermediate values.

Alternatively, the cannula 60 may be sealed at its distal end, so that the filler material may be delivered only through the pores 65. Alternatively, a shaped tip 64 may be incorporated into the cannula's distal end, thus creating a seal therewith. Alternatively, the shaped tip may be specifically designed for allowing particular functionality. In exemplary embodiments, the shaped tip may be designed as a trocar, and/or a driller, and/or a reamer, thus enhancing bone access capabilities of the present invention.

The inner rod 66 comprises a handle 67 and a rod 68. When assembled, the distal tip of the inner rod and the proximal end of the shaped tip are close to one another (not shown), and optionally in contact. Alternatively, the handles 61 and 67 may be capable of being interconnected.

In an exemplary method of treatment (not shown), the assembled set is introduced into a vertebra until a preferred portion of the cannula's distal end has penetrated to the desired location. The inner rod is then withdrawn. The bone filler material may then be pressurized into the cannula towards its distal end. After injection, the cannula may be withdrawn from the body.

In an alternative embodiment shown in FIG. 6F, the fenestrated cannula 60 may be combined with a longitudinal sleeve cover 110. Alternatively, the cannula and the sleeve cover may be connected at least to one point and/or a curve and/or an area. They may be alternatively connected at least at their distal tips. Another alternative may be to crimp the tips together.

In another embodiment of the invention, the sleeve cover may be at least partially made from a mesh structure (e.g. knitted/weaved fabric) and/or from a perforated membrane. If a mesh structure is used, it may be appropriate to use fibers having good resistance to tensile strength (e.g. stainless steel, high performance synthetic fibers, etc). Other biocompatible fibers, such as plastic (e.g. PMMA) fibers, may also be used.

When the bone filler material is injected into the bone using the injection device described herein, the sleeve cover is expanded before and/or during extrusion of the bone filler material into its surroundings. Injection of the bone filler material by embodiments of the present invention promotes homogeneous interdigitation within the bone and/or around the perforated segment.

Example 2

Delivering Material Through a Loose Longitudinal Sleeve

FIGS. 7A-7D show another exemplary set of instruments that can be used for VCF treatment. The set comprises a cannula 120 (shown in FIG. 7A), a longitudinal sleeve 71 (shown in FIG. 7B), an injection needle 74 (shown in FIG. 7C) and a stylet 75 (shown in FIG. 7D).

The cannula 120 comprises a handle 121 and a body 122 and may be made of any rigid biocompatible material (e.g. stainless steel). Preferably, the cannula body 122 is long enough to reach the inner volume of a vertebra during posterior and/or anterior surgeries. In one exemplary embodiment of the invention, the cannula body 122 is longer than about 50 mm, or longer than about 100 mm, or longer than about 150 mm. Alternatively, the cannula body may be approximately 120 mm long. In one exemplary embodiment of the invention, the cannula body has an outer diameter of about 2 mm, or about 4 mm, or about 6 mm, or lesser, or greater, or of intermediate values. Alternatively, the outer diameter of the cannula body may be approximately 4.2 mm. Alternative, the inner diameter of the cannula body may be smaller from its outer diameter by about 0.1 mm, or about 0.5 mm, or about 2 mm. Alternatively, the inner diameter of the cannula body may be about 3.6 mm.

The sleeve 71 comprises a handle 73 and a body 72. In one exemplary embodiment of the invention, the sleeve body 72 may be at least partially made from a mesh structure (e.g. knitted/weaved fabric) and/or a perforated membrane. If a mesh structure is used, it is most appropriate to use fibers having a good resistance to tensile strength (e.g. stainless steel, high performance synthetic fibers, etc). Other biocompatible fibers, such as PMMA fibers, may also be used. Alternatively, the sleeve handle may be coupled to the guiding cannula handle 121.

Alternatively, the injection needle 74 may be longer than the cannula body 122. The stylet 75 may be alternatively longer than the needle 74. Preferably, when the stylet is introduced into the sleeve, it may be capable of stretching the sleeve 71 to a predetermined length along its longitudinal axis, and optionally through injection needle 74 to the inner lumen. Optionally, said delivery system further includes an advance mechanism, capable of advancing and/or withdrawing the sleeve within the guiding cannula along its lumen.

In an embodiment of the invention, the advance mechanism may include at least two interconnected elements that permit relative uni-axial motion between them (e.g., a bolt-nut mechanism). For example, one element (e.g., a nut) may be fixed to the proximal end of the guiding cannula, and a second element (e.g., a mating bolt) may be connected to the proximal side of the sleeve. In that manner, the sleeve may travel distally or proximally, according to the set relative motion between the at least two interconnected elements.

The following steps are part of a complete exemplary procedure. At least a portion of these steps may be an exemplary embodiment of method of the invention. An example of steps for filling bone voids is:

(1) Positioning a patient for penetrating the guiding cannula 120 into a vertebra;

(2) Inserting a stylet 75 within an injection needle 74 which is within a sleeve 71 in a cannula 120 until at least part of the distal end of the sleeve is emerging out of the distal opening of the cannula 120 (as shown in FIG. 7E);

(3) Withdrawing the stylet out of the body (shown in FIG. 7F);

(4) Optionally, partly withdrawing the injection needle to a preferred position, so that a preferred length of the distal end of the sleeve loosely settles within the vertebra (not shown);

(5) Introducing bone filler material under pressure into the injection needle so that the material is urged towards the distal end of the sleeve. The filler material should be viscous enough and/or the pressure applied should be high enough and/or the pressure impact should be sufficient so that the distal end of the sleeve may expand to a predetermined preferred dimension and/or size and/or configuration (as shown in FIG. 7G). Preferably, the maximal diameter of the expanded part of the sleeve should be larger than the inner diameter of the guiding cannula. Alternatively, the maximal diameter may be greater than about 5 mm, or greater than about 10 mm, or greater than about 20 mm. The maximal diameter may alternatively be about 15 mm. Preferably, the force applied by the expanded part of the sleeve to its surroundings is high enough to move the opposing endplates of the vertebra apart. Alternatively, at least a small quantity of the filler material may extrude or flow through the meshed walls into the surroundings.

(6) Withdrawing the injection needle out of the body. Optionally, a preferred minimal pressure may be sustained within guiding the cannula and/or the sleeve. Alternatively, this step may be accomplished after the filler material has cured to a preferred higher average viscosity than it was during the injection step, although preferably, it has not yet totally solidified.

(7) Withdrawing the sleeve out of the body while extracting at least part of the remaining bone filler material through its meshed walls (as shown in FIG. 7H). Preferably, when the expanded part of the sleeve has maximal diameter within the vertebra and when it is larger than the inner diameter of the guiding cannula, at least part of the filler material that is entrapped therein is extruded when the sleeve 71 is extracted through the cannula.

(8) Withdrawing the guiding cannula out of the body.

Example 3

Delivering Material Through a Reinforced Longitudinal Sleeve

FIGS. 8A-8C show an exemplary set of instruments that can be used for VCF treatment. The set comprises a cannula 120 (shown in FIG. 8A), an injection element 80 (shown in FIG. 8B), and a stylet 83 (shown in FIG. 8C).

The cannula 120 comprises a handle 121 and a body 122 and may be made of any rigid biocompatible material (e.g. stainless steel). Preferably, the cannula body 122 is long enough to reach the inner volume of a vertebra during posterior and/or anterior surgeries. In one exemplary embodiment of the invention, the cannula body is longer than about 50 mm, or longer than about 100 mm, or longer than about 150 mm. Alternatively, the cannula body may be about 120 mm long. In one exemplary embodiment of the invention, the cannula body may have an outer diameter of about 2 mm, or about 4 mm, or about 6 mm, or lesser, or greater, or of intermediate values. Alternatively, the outer diameter of the cannula body 122 may be approximately 4.2 mm. Alternatively, the inner diameter of the cannula body 122 may be smaller than its outer diameter by about 0.1 mm, or by about 0.5 mm, or by about 2 mm. The inner diameter of the cannula body may alternatively be about 3.6 mm.

The injection element 80 comprises a relatively rigid injection needle 81, covering the sleeve 82 and the sleeve handle 84. Alternatively, the injection needle 81 may be coupled to the covering sleeve 82 in at least one spot and/or curve and/or area. Alternatively, they may be coupled to one another at least at their related proximal sides. In one exemplary embodiment of the invention, the covering sleeve 82 may be at least partially made from a mesh structure (e.g. knitted/weaved fabric) and/or a perforated membrane. If a mesh structure is used, it is most appropriate to use fibers having good resistance to tensile strength (e.g. stainless steel, high performance synthetic fibers, etc). Other biocompatible fibers, such as PMMA fibers, may be used also. Optionally, the sleeve handle 84 may be coupled to the guiding cannula handle 121.

The longitudinal body/bodies of the extraction mechanism should be preferably capable of withstanding sufficient tension force needed to overcome existing inner-pressure, drag force, compressive force, or any other combination of forces, in order to re-collapse and extract the permeable element out of the vertebral body, while still being able to force a sufficient quantity of bone void filler through the permeable element wall into the vertebral body. In one embodiment of the invention, the longitudinal body/bodies may be capable of withstanding sufficient compression force for forcing the permeable element into the vertebral body through the guiding cannula. In another embodiment of the invention, the longitudinal body may be the form of a rigid rod. In another embodiment of the invention, the longitudinal body may be in the form of wire or thread.

The injection needle 81 may alternatively be longer than the cannula body. The stylet 83 may alternatively be longer than the needle 81. Preferably, the stylet is capable of stretching the sleeve 82 to a predetermined length along its longitudinal axis when the stylet is introduced therein, optionally through the inner lumen of the injection needle.

The following steps are part of a complete exemplary procedure. At least a portion of these steps may be an exemplary embodiment of method of the invention. An example of steps for filling bone voids is:

(1) Positioning a patient for penetrating the guiding cannula 120 into a vertebra;

(2) Inserting the stylet 83 within the injection needle 81 of the injection element 80 within the cannula 120 until at least part of the distal end of the sleeve 82 is emerging out of the distal opening of the cannula (as shown in FIG. 8D);

(3) Withdrawing the stylet out of the body;

(4) Introducing bone filler material under pressure into the injection needle of the injection element. The bone filler material should be viscous enough and/or the pressure applied should be high enough and/or the pressure impact should be sufficient so that the distal end of the sleeve may expand to a predetermined preferred dimension and/or size and/or configuration (as shown in FIG. 8E). Preferably, the maximal diameter of the expanded part of the sleeve is larger than the inner diameter of the guiding cannula. Alternatively, the maximal diameter may be greater than about 5 mm, or greater than about 10 mm, or greater than about 20 mm. The maximal diameter may alternatively be about 15 mm. Preferably, the force applied by the expanded part of sleeve to its surroundings may be high enough to move the opposing endplates of the vertebra apart. Alternatively, at least a small quantity of the filler material may extrude or flow through the meshed walls into the surroundings.

(5) Withdrawing the injection element out of the body while extracting at least part of the remaining bone filler material through its meshed walls (as shown in FIG. 8G). Preferably, when the expanded part of the sleeve has maximal diameter within vertebra and when it is larger than the inner diameter of the guiding cannula, at least part of the filler material that is entrapped therein is extruded when the injection element is extracted through the cannula.

(6) Withdrawing the guiding cannula out of the body.

Using the Exemplary Bone Access Kit

FIGS. 9A-9C show an exemplary set of instruments, at least a portion of which may be used as a part of a bone access kit for accessing or penetrating a vertebra. The penetration may include using a posterior and/or an anterior approach. The set comprises a guiding cannula 120 (shown in FIG. 9A), a hollow drill 90 (not shown), and/or a regular drill 91 (shown in FIG. 9B), and an optional guide wire 92 (shown in FIG. 9C).

In one exemplary embodiment of the invention, the instruments may be part of a complete kit for accessing a bone and delivering bone filler material therein. For example, they may be used during a vertebroplasty procedure, when preferably, at least one of the other exemplary tools of the invention is added.

Preferably, the guiding cannula may be later used for guiding the injection element containing bone filler material towards the vertebra. The cannula comprises a handle 121 and a body 122 and may be made of any rigid biocompatible material (e.g. stainless steel). Preferably, the cannula body may be long enough to reach the inner volume of a vertebra during posterior and/or anterior surgeries. In one embodiment of the invention, the cannula body may be longer than about 50 mm, or longer than about 100 mm, or longer than about 150 mm. The cannula body may be alternatively about 120 mm long. In one embodiment of the invention, the cannula body may have an outer diameter of about 2 mm, or about 4 mm, or about 6 mm, or lesser, or greater, or of an intermediate value. Alternatively, the outer diameter of the cannula body may be about 4.2 mm. Alternatively, the inner diameter of the cannula body may be smaller than its outer diameter by about 0.1 mm, or by about 0.5 mm, or by about 2 mm. The inner diameter of the cannula body may alternatively be about 3.6 mm.

The drills that are used in this procedure should preferably be rigid enough when they are inserted into the cannula lumen that they may be capable of protruding out of the lumen. This is so their drilling/reaming tips may properly be used for accessing, and/or penetrating, and/or carving into the bone.

The guide wire may be any commercially available guide wire, capable of threading through the hollow drill.

The following steps are part of a complete exemplary procedure. At least a portion of these steps may be an exemplary embodiment of method of the invention. An example of steps for filling bone voids is:

(1) The optional step of inserting the guide wire into the body to a preferred location (not shown);

(2) Inserting the regular drill and/or the hollow drill, which has been assembled within the cannula (as shown in FIG. 9D), into the body. Alternatively, if the hollow drill has been used, after performing step (1) above, the hollow drill may be passed through the guide wire.

(3) The optional step of withdrawing the guide wire from the body (not shown).

(4) Using the drill for accessing the bone (e.g., the vertebra) and penetrating there. Preferably, at least part of the guiding cannula should penetrate into the vertebra for the later optional delivery of the bone filler material as previously described other embodiments of the invention.

(5) Withdrawing the drill from the body (not shown).

An Example of an Alternative Extraction Kit

If at least part of a mesh structure is unable to be extracted out of the bone (e.g., vertebra) under reasonable force, an alternative method may be applied so that the procedure may still be completed appropriately. One optional procedure is to tear a part of the mesh structure off from the whole so as to let it remain within the bone. In this case, the torn portion to the mesh structure may be considered as an implant which is combined with the solidified filler material within the bone structure. Alternatively, at least part of the sleeve or mesh bag may be cut by using a cutting tool specially designed for this purpose.

If at least part of the sleeve or mesh is to be left within the bone structure, the stylet and the injection needle are first removed. As the extractor is removed, the mesh is left within the guiding cannula. The cannula is then removed leaving only the mesh itself. A proximal loose end of the bag may be then cut off with a knife or surgical scissors thus leaving its distal end together with the hardened cement therein within the body. Such a procedure is recommended when it becomes impossible to remove the mesh or bag without damage to the patient.

Further Exemplary Embodiment

Figure 10A:
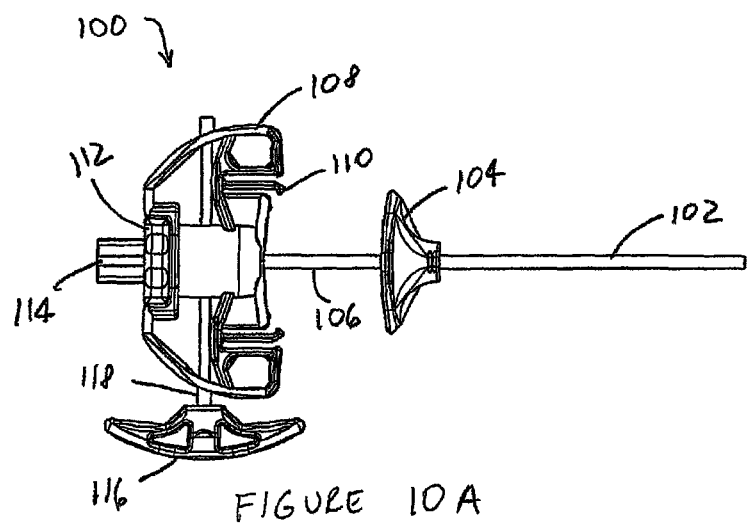
FIG. 10A is a side view of an embodiment of the mesh assembly of the present invention.

FIG. 10A illustrates a preferred embodiment of a mesh assembly 100 inserted into a working cannula 102. In this example, it is to be understood that the working cannula would be previously inserted and properly located within bone of the patient. The working cannula has a handle 104 for ease of control. The mesh assembly 100, has a shaft 106. The shaft 106 is the longitudinal sleeve, covering both the needle tube and the stylet. It is shown as partially inserted into the bore of the working cannula. The mesh assembly has a handle 108 which, in turn, has engagement elements 110 extending therefrom. The engagement elements are adapted for engaging and releasably securing the handle of the cannula thereto. Such engagement elements may be, for example, detents or other elements.

The mesh assembly illustrated in FIGS. 10A and 10B includes both the mesh and an injection needle and is shown with the injection needle secured therein so that only the handle 112 of the injection needle appears. The needle tube is located within the longitudinal sleeve 106. The tube of the injection needle, together with the stylet, stretches the mesh assembly distally. The injection needle is secured to the handle of the mesh assembly, for example, by having threads which screw therein. Similarly, the stylet is also secured by threads therein so that only its knurled knob 114 may be seen in these figures. A rotating handle 116 having a shaft 118 is depicted extending through the handle of the mesh assembly.

The permeable element or mesh is preferably a porous fabric made into a collapsible sack-like arrangement. It is inserted into the bone to be filled through the working cannula. Preferably, it should protrude therein about 20 mm. The mesh is preferably mounted on the stylet. The stylet should preferably have a blunt leading edge. Alternatively, the extraction mechanism and the permeable element may be combined in a single instrument.

Figure 11B:
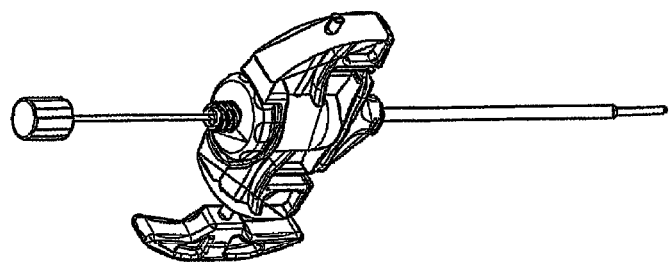
FIG. 11B is an isometric view of the embodiment shown in FIG. 11A.
Figure 11A:
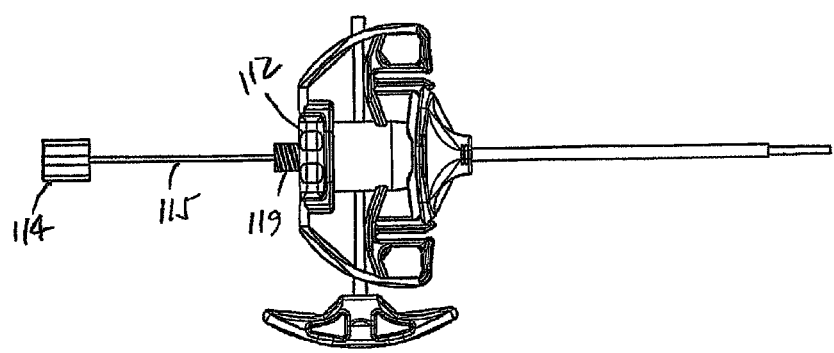
FIG. 11A is a side view of an embodiment of the present invention showing the removal of the stylet.

As illustrated in FIGS. 11A and 11B, when the mesh assembly has been secured to the handle of the properly placed working cannula, preparatory to a cement delivery system being connected to the mesh assembly, the stylet should first be removed. As shown in FIGS. 11A and 11B, the stylet has a shaft 115. As can now be seen in these figures, the knurled knob of the stylet is adapted to engage the threads 119 which extend from the handle 112 of the injection needle. As can also be seen in these figures, the handle of the mesh assembly has been secured to the handle of the working cannula. One main purpose of the stylet is to give extra rigidity for the cannula-mesh assembly and to stretch the sleeve so it will protrude out of cannula distal opening and be located within the vertebra. Afterwards, the stylet should be removed for injecting the bone cement.

Figure 12A:
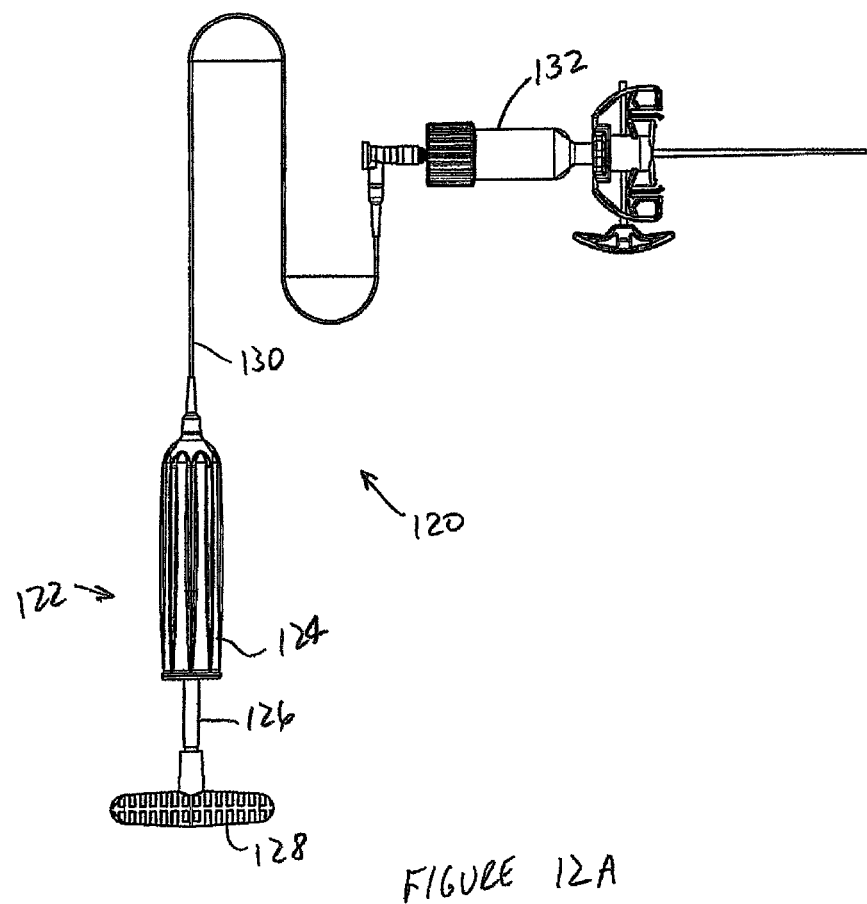
FIG. 12A is a side view of an embodiment of the present invention showing the cement injection assembly.
Figure 12B:
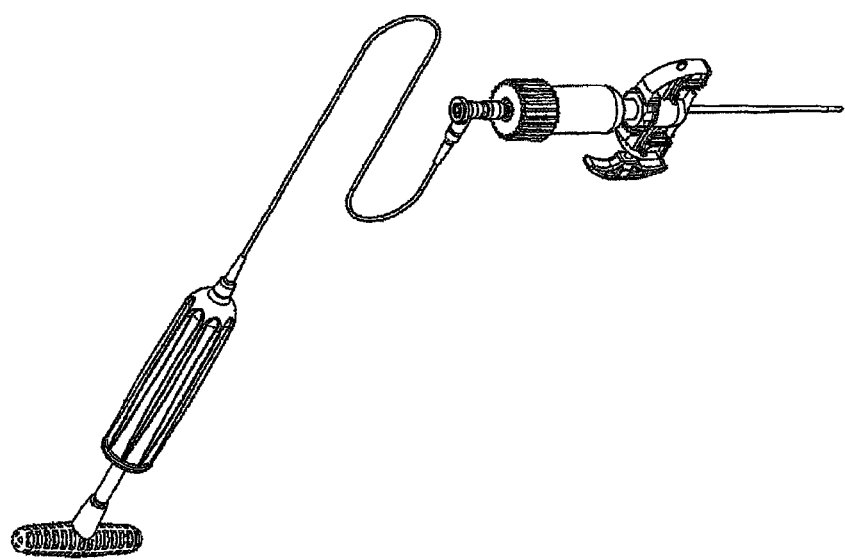
FIG. 12B is an isometric view of the embodiment shown in FIG. 12A.
Figure 13B:
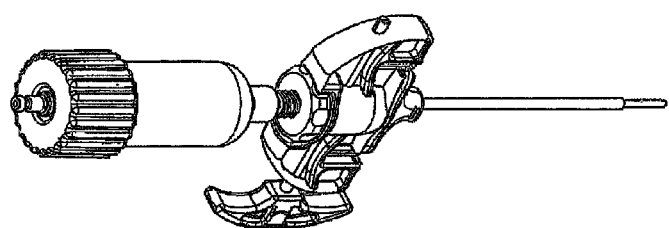
FIG. 13B is an isometric view of the embodiment shown in FIG. 13A.
Figure 13A:
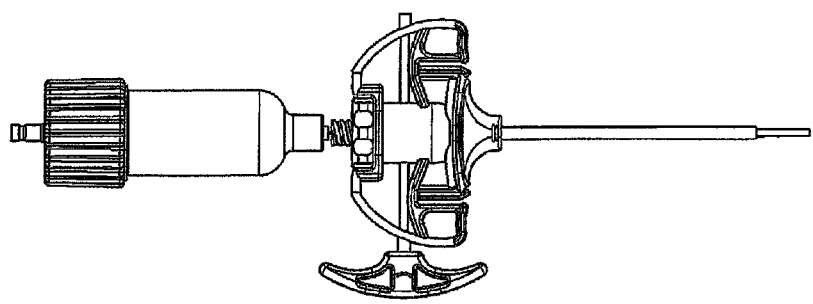
FIG. 13A is a side view of an embodiment of the present invention showing disconnecting the reservoir.

As illustrated in FIGS. 12A and 12B, after the stylet has been removed, a cement delivery system 120 may be connected to the threads of the injection needle. The cement delivery system comprises a plunger 122, which is essentially a cylinder 124 having a piston therein. Extending from the piston is a rod 126 having a handle 128 connected thereto. A pressurizing line 130 is connected to the cylinder of the plunger for providing pressure for injecting cement to the bone of the patient. A reservoir 132 having a floating piston therein (not shown) is depicted attached to the threads of the injection needle. The reservoir is preferably pre-filled with the prepared cement. The cement is then inserted into the bone of the patient by the pressure supplied by the plunger 122. This pressure forces the floating piston positioned within the reservoir 132 to move distally. Injection of the bone filler material by embodiments of the present invention promotes homogeneous interdigitation within the bone and/or around the perforated segment. Preferably, when the amount of injected cement is sufficient, as verified by, for example, fluoroscopy, then the cement delivery system may be removed. FIGS. 13A and 13B depict the disconnection of the cement delivery system from the mesh assembly.

Figure 14B:
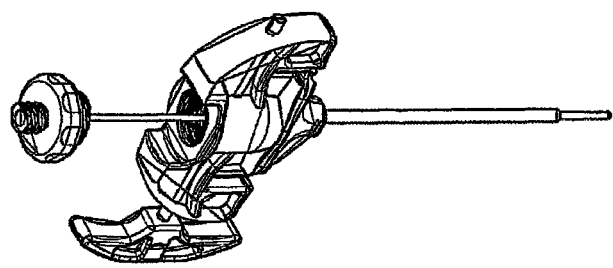
FIG. 14B is an isometric view of the embodiment shown in FIG. 14A.
Figure 14A:
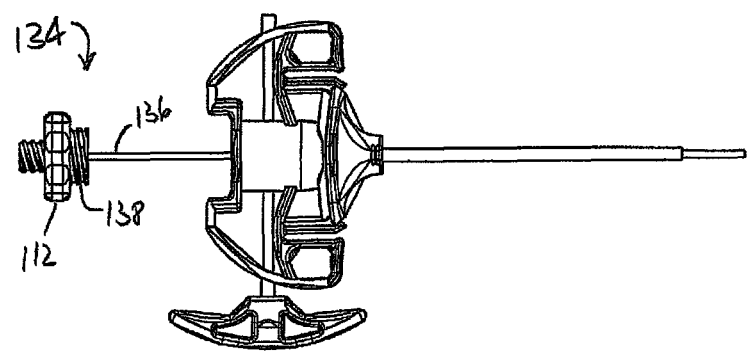
FIG. 14A is a side view of an embodiment of the present invention showing removing the injection cannula.

As illustrated in FIGS. 14A and 14B, after the cement delivery system has been removed from the mesh assembly, the injection needle may be removed. As can now be seen in these figures, the injection needle 134 has a shaft 136 that is adapted to fit within the bore of the working cannula. As can also be seen in these figures, the injection needle may be secured to the handle of the mesh assembly, for example, by threads 138 adapted for engaging therewith.

Figure 15B:
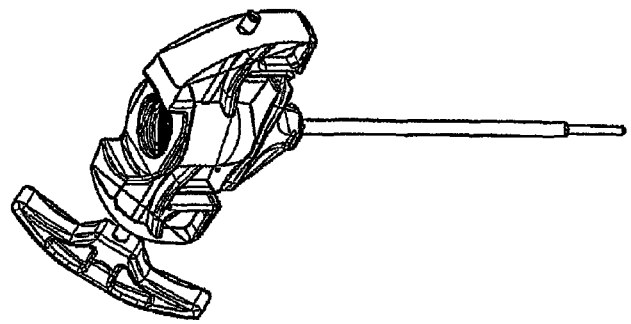
FIG. 15B is an isometric view of the embodiment shown in FIG. 15A.
Figure 15A:
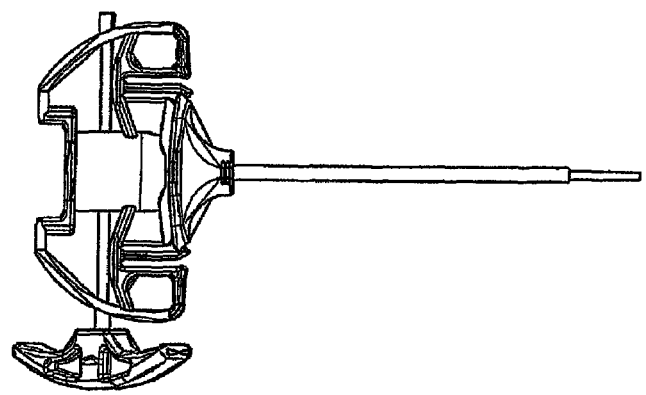
FIG. 15A is a side view of an embodiment of the present invention showing the rotational handle of the mesh assembly.

FIGS. 15A and 15B depict the rotational handle of the mesh assembly. After the injection needle has been removed from the handle of the mesh assembly, the mesh is preferably extracted from the patient. The mesh is extracted by rotating the rotational handle until it is preferably entirely removed.

Figure 16A:
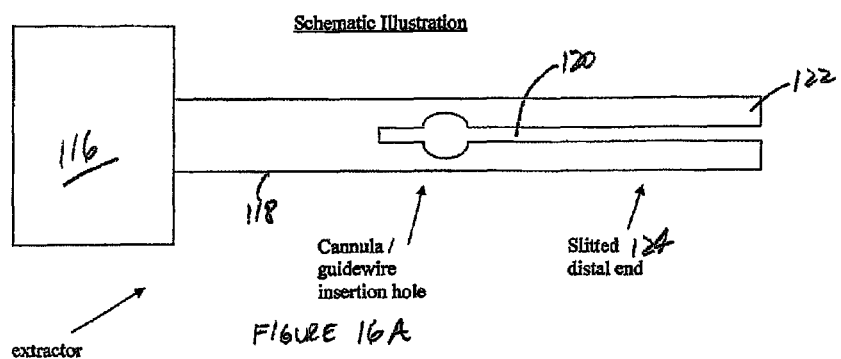
FIG. 16A is a schematic illustration of the extraction mechanism of FIG. 15B.
Figure 16B:
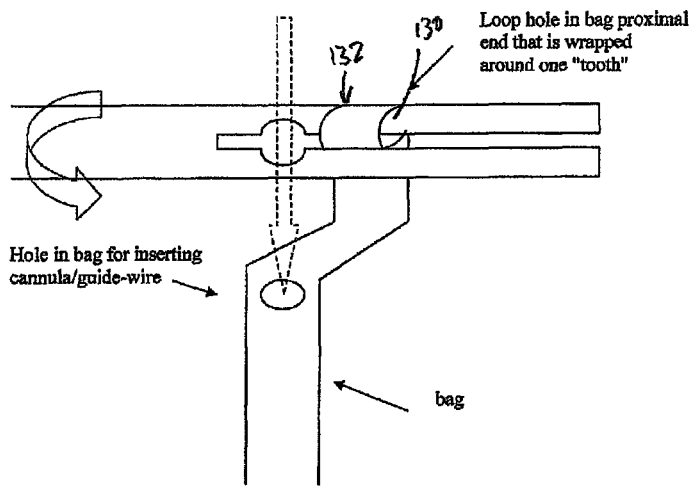
FIG. 16B is a schematic illustration of the embodiment shown in FIG. 16A showing the bag looped around the slitted distal end of the extraction mechanism of the present invention.

FIGS. 16A and 16B schematically illustrate the operational characteristics of the rotational handle and its engagement with the mesh and the handle of the mesh assembly. The shaft 118 of the rotational handle has a slot 120 extending at least a portion along its distal end 122 thereby creating a slitted distal end 124. As more particularly illustrated in FIG. 16B, the mesh bag which has been previously described preferably has a loop 130 at its proximal end 132. The loop 132 is adapted for engaging the slitted distal end 124 of the shaft of the rotational handle. Also shown in FIG. 16B is a hole 134 in the bag for allowing the insertion to the cannula or the guide wire therethrough.

Figure 17:
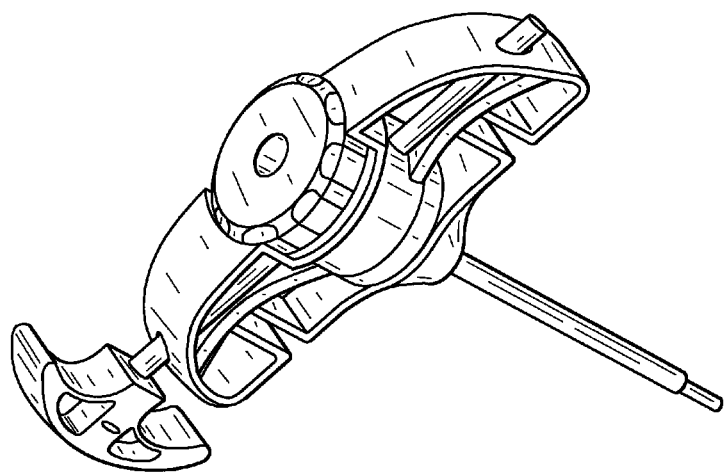
FIG. 17 is an exploded isometric view of the engagement of the handle with an end of the permeable element.

As illustrated in FIG. 17, which shows an exploded side view of the engagement of the rotational handle with the handle of the mesh assembly and the bag, when the rotational handle is rotated the bag is wound upon the shaft 118. In this way, when the rotational handle is rotated the bag may be pulled out of the bone of the patient. As the bag is pulled out of the bone of the patient, the cement material is extracted from the bag thus leaving the cement remaining within the bone. By extracting the permeable bag out of the bone in this manner, the pressure therein is increased. This forces the bone void filler material to penetrate the bag walls and flow through its pores into the cancellous bone and/or cavity in the bone. This promotes height restoration of the bone and introduces the bone filler material to the body in an enhanced controlled manner. As preferentially shown herein, the bag is coupled to only one "tooth" of the slitted distal end of the shaft. Thus, as the handle revolves, the bag wraps around both teeth.

Although the particular embodiments shown and described above will prove to be useful in many applications in the bone filling and the vertebral reconstruction art to which the present invention pertains, further modifications of the present invention will occur to persons skilled in the art. All such modifications are deemed to be within the scope and spirit of the present invention as defined by the appended claims.

The invention claimed is:

1. A device for filling a void in a patient's bone with bone void filler, comprising:
   a. a sleeve for receiving bone void filler;
   b. a cannula for extending into the bone and for guiding the sleeve to the void; and
   c. an elongate body insertable through the sleeve and configured to stretch the sleeve along a longitudinal axis thereof;
   wherein the sleeve is adapted for retaining most of the bone void filler therein until the sleeve is withdrawn from the cannula.

2. The device of claim 1, wherein said sleeve is permeable to the bone void filler so that the bone void filler may flow into the void when pressure is applied thereto.

3. The device of claim 1, further comprising an injection needle for extending into said sleeve for injecting the bone void filler therein.

4. The device of claim 1, further comprising a pressurizing device for delivering the bone void filler into said sleeve.

5. The device of claim 4, wherein said pressurizing device delivers pressure exceeding about 20 Atm.

6. The device of claim 4, wherein said pressurizing device delivers pressure exceeding about 100 Atm.

7. The device of claim 4, wherein said pressurizing device delivers pressure exceeding about 200 Atm.

8. The device of claim 1, wherein said sleeve comprises a mesh.

9. The device of claim 1, wherein said sleeve comprises a biocompatible material.

10. The device of claim 1, wherein the bone void filler sets into a hardened condition.

11. The device of claim 1, wherein the bone void filler is a non-setting material.

12. The device of claim 1, wherein said elongate body is a stylet.

13. The device of claim 8, wherein said mesh comprises metallic fibers.

14. The device of claim 8, wherein said mesh comprises synthetic fibers.

15. The device of claim 8, wherein said mesh comprises aramid fibers.

16. The device of claim 1, wherein the cannula includes a handle and a cannula body, and the elongate body is longer than the cannula body.

17. A method of introducing bone void filler into a void in a patient's bone, comprising:
   a. inserting a cannula into the bone;
   b. inserting a sleeve through the cannula into the bone;
   c. inserting an elongate body into the sleeve and stretching the sleeve in a substantially longitudinal direction;
   d. expanding the sleeve with bone void filler; and
   e. extruding the bone void filler into the bone void by extracting the sleeve through the cannula.

18. The method of claim 17, wherein the cannula has a passage therein having an inner diameter of about 2 mm or less.

19. The method of claim 17, wherein the cannula has a passage therein having an inner diameter of about 4 mm or less.

20. The method of claim 17, further comprising advancing the sleeve within the cannula using an advancing mechanism prior to expanding the sleeve with the bone void filler.

21. The method of claim 17, wherein the bone comprises a vertebra and expanding the sleeve with bone void filler moves opposing endplates of the vertebra apart.

22. A device for filling a void in a patient's bone with bone void filler, comprising:
   a. an injection element;
   b. an expandable sleeve having proximal and distal ends; and
   c. a cannula for extending into the bone and for guiding the sleeve to the void, the cannula having proximal and distal ends;
   wherein when the cannula and the sleeve are inserted into a patient, the proximal end of the sleeve is coupled to a proximal end of the cannula and the injection element is configured to inject bone void filler into the sleeve to expand the sleeve.

23. The device of claim 22, wherein the sleeve comprises a mesh.

24. The device of claim 22, further comprising a first advancing element coupled to a proximal end of the cannula and a second advancing element coupled to the proximal end of the sleeve for translating the sleeve relative to the cannula.

25. The device of claim 24, wherein the first advancing element comprises a nut and the second advancing element comprises a bolt.

26. The device of claim 22, wherein when the distal end of the sleeve extends into the void, the proximal end of the cannula and the proximal end of the sleeve are positioned outside of the patient's body.

* * * * *